United States Patent
Clark et al.

(10) Patent No.: US 10,441,155 B2
(45) Date of Patent: Oct. 15, 2019

(54) MEDICAL DEVICES WITH BATTERY REMOVAL

(71) Applicant: OBP Medical Corporation, Lawrence, MA (US)

(72) Inventors: Adrienne Clark, Waltham, MA (US); Demetrio Donald Anaya, Somerville, MA (US); Nick Lauder, Medford, MA (US)

(73) Assignee: OBP Medical Corporation, Lawrence, MA (US)

( * ) Notice: Subject to any disclaimer, the term of this patent is extended or adjusted under 35 U.S.C. 154(b) by 0 days.

(21) Appl. No.: 16/139,813

(22) Filed: Sep. 24, 2018

(65) Prior Publication Data
US 2019/0117042 A1     Apr. 25, 2019

Related U.S. Application Data

(60) Provisional application No. 62/649,190, filed on Mar. 28, 2018, provisional application No. 62/574,969, (Continued)

(51) Int. Cl.
*A61B 1/267* (2006.01)
*A61B 1/32* (2006.01)
(Continued)

(52) U.S. Cl.
CPC ............ *A61B 1/32* (2013.01); *A61B 1/00032* (2013.01); *A61B 1/00066* (2013.01);
(Continued)

(58) Field of Classification Search
CPC .......................................... A61B 1/267–1/317
See application file for complete search history.

(56) References Cited

U.S. PATENT DOCUMENTS

| 559,122 A | 4/1896 | Daily |
|---|---|---|
| 2,235,979 A | 3/1941 | Brown |

(Continued)

FOREIGN PATENT DOCUMENTS

| CN | 2239235 Y | 11/1996 |
|---|---|---|
| CN | 2265156 Y | 10/1997 |

(Continued)

OTHER PUBLICATIONS

European Search Report dated Nov. 23, 2018, which is enclosed, that issued in the corresponding European Patent Application No. 16747107.7.

(Continued)

*Primary Examiner* — Eduardo C Robert
*Assistant Examiner* — Michelle C Eckman
(74) *Attorney, Agent, or Firm* — Cowan, Liebowitz & Latman, P.C.

(57) ABSTRACT

A battery-powered medical device comprising: an outer housing having an opening formed therein; a power source housed within the outer housing, the outer housing being configured to at least partially enclose the power source so as to prevent contamination of the power source with biohazardous materials, the power source being removable from the outer housing via the opening; and a cover configured to cover the opening in the outer housing and to retain the power source within the outer housing, wherein the cover is configured to be operated by a user to expose the opening in the outer housing, when the cover is operated to expose the opening, the outer housing is configured to release the power source via the opening without requiring physical contact between the user and the power source, and when the cover is operated to expose the opening, the outer housing is configured to provide a direct path for release of
(Continued)

the power source via the opening, such path providing no contact with contaminated surfaces of the medical device.

28 Claims, 24 Drawing Sheets

Related U.S. Application Data filed on Oct. 20, 2017, provisional application No. 62/574,412, filed on Oct. 19, 2017.

(51) Int. Cl.
*A61B 1/00* (2006.01)
*A61B 17/02* (2006.01)
*A61B 1/31* (2006.01)
*A61B 1/303* (2006.01)
*A61B 1/06* (2006.01)
*A61B 17/00* (2006.01)

(52) U.S. Cl.
CPC ........ *A61B 1/00108* (2013.01); *A61B 1/0684* (2013.01); *A61B 1/267* (2013.01); *A61B 1/303* (2013.01); *A61B 1/31* (2013.01); *A61B 17/02* (2013.01); *A61B 2017/00734* (2013.01)

(56) References Cited

U.S. PATENT DOCUMENTS

| | | | |
|---|---|---|---|
| 2,247,458 | A | 6/1941 | Shepard |
| 2,482,971 | A | 9/1949 | Golson |
| 2,592,190 | A | 4/1952 | Rubens et al. |
| 3,324,850 | A | 6/1967 | Gunning et al. |
| 3,332,414 | A | 7/1967 | Gasper |
| 3,426,749 | A * | 2/1969 | Jephcott ............ A61B 1/00142 206/363 |
| 3,532,088 | A | 10/1970 | Fiore |
| 3,592,199 | A | 7/1971 | Ostensen |
| 3,595,222 | A | 7/1971 | Vellacott |
| 3,598,113 | A * | 8/1971 | Moore ............... A61B 1/00103 385/117 |
| 3,638,644 | A | 2/1972 | Reick |
| 3,675,641 | A | 7/1972 | Fiore |
| 3,716,047 | A | 2/1973 | Moore et al. |
| 3,729,006 | A | 4/1973 | Wilder et al. |
| 3,762,400 | A | 10/1973 | McDonald |
| 3,769,968 | A | 11/1973 | Blount et al. |
| 3,789,835 | A | 2/1974 | Whitman |
| 3,815,585 | A | 6/1974 | Fiore |
| 3,826,248 | A | 7/1974 | Gobels |
| 3,851,642 | A | 12/1974 | McDonald |
| 3,934,578 | A | 1/1976 | Heine |
| 3,945,371 | A | 3/1976 | Adelman |
| 3,978,850 | A | 9/1976 | Moore et al. |
| 4,067,323 | A | 1/1978 | Troutner |
| 4,156,424 | A | 5/1979 | Burgin |
| 4,210,133 | A | 7/1980 | Castaneda |
| 4,226,228 | A | 10/1980 | Shin et al. |
| 4,263,899 | A | 4/1981 | Burgin |
| 4,300,541 | A | 11/1981 | Burgin |
| 4,337,763 | A | 7/1982 | Petrassevich |
| 4,432,351 | A | 2/1984 | Hoary |
| 4,492,220 | A | 1/1985 | Hayes |
| 4,502,468 | A | 3/1985 | Burgin |
| 4,527,553 | A | 7/1985 | Upsher |
| 4,546,761 | A | 10/1985 | McCullough |
| 4,562,832 | A | 1/1986 | Wilder |
| 4,566,439 | A | 1/1986 | Burgin |
| 4,574,784 | A | 3/1986 | Soloway |
| 4,596,239 | A * | 6/1986 | Bauman ............ A61B 1/0669 362/204 |
| 4,597,383 | A | 7/1986 | Van Der Bel |
| 4,607,623 | A | 8/1986 | Bauman |
| 4,619,248 | A | 10/1986 | Walsh |
| 4,638,792 | A | 1/1987 | Burgin |
| 4,766,887 | A | 8/1988 | Cecil, Jr. et al. |
| 4,807,600 | A | 2/1989 | Hayes |
| 4,884,559 | A | 12/1989 | Collins |
| 4,901,708 | A * | 2/1990 | Lee ................. A61B 1/267 600/138 |
| 4,905,670 | A | 3/1990 | Adair |
| 4,934,352 | A | 6/1990 | Sullivan, Jr. |
| 4,971,036 | A | 11/1990 | Collins |
| 5,018,507 | A | 5/1991 | Montaldi |
| 5,026,368 | A | 6/1991 | Adair |
| 5,054,906 | A | 10/1991 | Lyons, Jr. |
| 5,063,908 | A | 11/1991 | Collins |
| 5,143,054 | A | 9/1992 | Adair |
| 5,165,387 | A | 11/1992 | Woodson |
| 5,174,278 | A | 12/1992 | Babkow |
| 5,179,937 | A | 1/1993 | Lee |
| 5,179,938 | A | 1/1993 | Lonky |
| 5,222,271 | A | 6/1993 | Eganhouse |
| D337,384 | S | 7/1993 | Schucman |
| 5,318,009 | A | 6/1994 | Robinson |
| 5,329,938 | A | 7/1994 | Lonky |
| 5,427,152 | A | 6/1995 | Weber |
| 5,438,976 | A | 8/1995 | Nash |
| 5,465,709 | A | 11/1995 | Dickie et al. |
| 5,499,964 | A | 3/1996 | Beck et al. |
| 5,512,038 | A | 4/1996 | O'Neal et al. |
| 5,695,492 | A | 12/1997 | Brown |
| 5,716,329 | A | 2/1998 | Dieter |
| 5,785,648 | A | 7/1998 | Min |
| 5,840,013 | A | 11/1998 | Lee et al. |
| 5,846,249 | A | 12/1998 | Thompson |
| 5,865,729 | A | 2/1999 | Meehan |
| 5,873,820 | A | 2/1999 | Norell |
| 5,879,304 | A | 3/1999 | Schuchman et al. |
| 5,888,195 | A | 3/1999 | Schneider |
| 5,899,854 | A | 5/1999 | Slishman |
| 5,916,150 | A | 6/1999 | Sillman |
| 6,004,265 | A | 12/1999 | Hsu et al. |
| 6,036,638 | A | 3/2000 | Nwawka |
| 6,036,713 | A | 3/2000 | Kieturakis |
| 6,048,308 | A | 4/2000 | Strong |
| 6,080,105 | A | 6/2000 | Spears |
| 6,130,520 | A | 10/2000 | Wawro et al. |
| 6,176,824 | B1 | 1/2001 | Davis |
| 6,186,944 | B1 | 2/2001 | Tsai |
| 6,217,512 | B1 | 4/2001 | Salo et al. |
| 6,231,505 | B1 | 5/2001 | Martin |
| 6,254,247 | B1 | 7/2001 | Carson |
| 6,277,067 | B1 | 8/2001 | Blair |
| 6,319,199 | B1 | 11/2001 | Sheehan et al. |
| 6,346,085 | B1 | 2/2002 | Schiffman |
| 6,359,644 | B1 | 3/2002 | Salvati |
| 6,361,489 | B1 | 3/2002 | Tsai |
| 6,379,296 | B1 | 4/2002 | Baggett |
| 6,379,299 | B1 | 4/2002 | Borodulin et al. |
| 6,394,111 | B1 | 5/2002 | Jacobs et al. |
| 6,394,950 | B1 | 5/2002 | Weiss |
| 6,416,465 | B2 | 7/2002 | Brau |
| 6,428,180 | B1 | 8/2002 | Karram et al. |
| 6,432,045 | B2 | 8/2002 | Lemperle et al. |
| 6,432,049 | B1 | 8/2002 | Banta |
| 6,436,033 | B2 | 8/2002 | Tan |
| 6,450,952 | B1 | 9/2002 | Rioux |
| 6,468,206 | B1 | 10/2002 | Hipps et al. |
| 6,468,232 | B1 | 10/2002 | Ashton-Miller et al. |
| 6,487,440 | B2 | 11/2002 | Deckert et al. |
| 6,504,985 | B2 | 1/2003 | Parker et al. |
| 6,523,973 | B2 | 2/2003 | Galli |
| 6,524,259 | B2 | 2/2003 | Baxter-Jones et al. |
| 6,569,091 | B2 | 5/2003 | Diokno et al. |
| 6,589,168 | B2 | 7/2003 | Thompson |
| 6,595,917 | B2 | 7/2003 | Nieto |
| 6,616,603 | B1 | 9/2003 | Fontana |
| 6,626,825 | B2 | 9/2003 | Tsai |
| 6,663,576 | B2 | 12/2003 | Gombrich et al. |
| 6,676,598 | B2 | 1/2004 | Rudischhauser et al. |
| 6,719,688 | B2 | 4/2004 | Pecherer et al. |
| 6,761,687 | B1 | 7/2004 | Doshi |

(56) References Cited

U.S. PATENT DOCUMENTS

| | | |
|---|---|---|
| 6,830,547 B2 | 12/2004 | Weiss |
| 6,896,653 B1 | 5/2005 | Vail, III et al. |
| 7,014,340 B2 | 3/2006 | Betis |
| 7,029,439 B2 | 4/2006 | Roberts et al. |
| D520,464 S | 5/2006 | Strong |
| 7,223,223 B2 | 5/2007 | Lindsay |
| 7,276,025 B2 | 10/2007 | Roberts et al. |
| 7,306,559 B2 | 12/2007 | Williams |
| 7,631,981 B2 | 12/2009 | Miller et al. |
| 7,736,304 B2 | 6/2010 | Pecherer |
| 7,758,203 B2 | 7/2010 | McMahon et al. |
| 7,878,973 B2 | 2/2011 | Yee et al. |
| 7,909,759 B2 | 3/2011 | Pecherer |
| 7,967,809 B2 | 6/2011 | Jay-Robinson |
| 8,012,089 B2 | 9/2011 | Bayat |
| 8,047,987 B2 | 11/2011 | Grey et al. |
| 8,088,066 B2 | 1/2012 | Grey et al. |
| 8,096,945 B2 | 1/2012 | Buchok et al. |
| 8,142,352 B2 | 3/2012 | Vivenzio et al. |
| 8,142,353 B2 | 3/2012 | Pecherer et al. |
| 8,157,728 B2 | 4/2012 | Danna et al. |
| 8,162,826 B2 | 4/2012 | Pecherer et al. |
| 8,251,898 B2 | 8/2012 | Pecherer |
| 8,317,693 B2 | 11/2012 | Grey et al. |
| 8,388,523 B2 | 3/2013 | Vivenzio et al. |
| 8,394,017 B2 | 3/2013 | Kieffer |
| 8,435,175 B2 | 5/2013 | McMahon et al. |
| 8,512,234 B2 | 8/2013 | Grey et al. |
| 8,512,237 B2 | 8/2013 | Bastia |
| 8,555,892 B2 | 10/2013 | Traub |
| 8,596,847 B2 | 12/2013 | Vayser et al. |
| 8,628,879 B2 | 1/2014 | Pecherer et al. |
| 8,821,385 B2 | 9/2014 | Naito |
| D719,652 S | 12/2014 | Swift |
| 8,979,745 B2 | 3/2015 | Swift |
| 9,050,048 B2 | 6/2015 | Nadershahi |
| D745,669 S | 12/2015 | Swift |
| D752,217 S | 3/2016 | Swift |
| D753,295 S | 4/2016 | Vivenzio et al. |
| 9,307,897 B2 | 4/2016 | Swift |
| 9,332,898 B2 | 5/2016 | McMahon et al. |
| 9,532,706 B2 | 1/2017 | McMahon et al. |
| 9,629,529 B1 | 4/2017 | Indovina et al. |
| 9,718,130 B1 | 8/2017 | Vayser et al. |
| 9,763,743 B2 | 9/2017 | Lin et al. |
| 9,808,231 B2 | 11/2017 | Miraki et al. |
| 9,814,377 B2 | 11/2017 | Lia et al. |
| 9,820,638 B2 | 11/2017 | Cheng |
| 9,820,729 B2 | 11/2017 | Miles et al. |
| 9,826,892 B2 | 11/2017 | Dresher et al. |
| 9,833,295 B2 | 12/2017 | Vayser et al. |
| 9,844,364 B2 | 12/2017 | Grey et al. |
| 9,861,349 B2 | 1/2018 | Nadershahi et al. |
| 9,867,531 B2 | 1/2018 | Pacey et al. |
| 9,877,639 B2 | 1/2018 | Grey et al. |
| 9,877,644 B2 | 1/2018 | Greenstein et al. |
| D809,660 S | 2/2018 | Nguyen et al. |
| 9,883,792 B2 | 2/2018 | McMahon et al. |
| 9,888,957 B2 | 2/2018 | Wolf et al. |
| 9,907,544 B2 | 3/2018 | Nadershahi et al. |
| 9,913,682 B2 | 3/2018 | Wolf et al. |
| 9,918,618 B2 | 3/2018 | Molnar |
| 9,918,802 B2 | 3/2018 | Coppersmith et al. |
| 9,931,028 B2 | 4/2018 | Lia et al. |
| 9,943,295 B2 | 4/2018 | King |
| 9,949,814 B2 | 4/2018 | Alexander et al. |
| 9,955,858 B2 | 5/2018 | Pamnani et al. |
| 9,968,262 B2 | 5/2018 | Greenstein et al. |
| 9,968,346 B2 | 5/2018 | Alexander et al. |
| 9,980,710 B2 | 5/2018 | Seifert et al. |
| 9,986,901 B2 | 6/2018 | Grey et al. |
| 9,986,903 B2 | 6/2018 | Nadershahi et al. |
| 9,986,988 B2 | 6/2018 | Ferro et al. |
| 9,999,345 B2 | 6/2018 | Vayser et al. |
| 10,004,392 B2 | 6/2018 | Millard et al. |
| 10,004,393 B2 | 6/2018 | Kucklick |
| 10,028,648 B2 | 7/2018 | Goldfain et al. |
| 10,028,649 B2 | 7/2018 | Salvati et al. |
| 10,028,780 B2 | 7/2018 | Wolf et al. |
| 10,045,686 B2 | 8/2018 | Ou Yang et al. |
| 10,045,731 B2 | 8/2018 | Prasad et al. |
| 10,052,432 B2 | 8/2018 | Dexter et al. |
| 10,064,611 B2 | 9/2018 | Ross et al. |
| 10,064,613 B2 | 9/2018 | Davis et al. |
| 10,068,173 B2 | 9/2018 | Vayser et al. |
| 10,092,176 B2 | 10/2018 | Kienzle et al. |
| 10,092,281 B2 | 10/2018 | Perler et al. |
| 10,098,530 B2 | 10/2018 | McMahon et al. |
| 10,105,043 B2 | 10/2018 | George |
| 10,117,646 B2 | 11/2018 | Friedrich et al. |
| 10,130,441 B2 | 11/2018 | Martinez |
| 10,166,016 B2 | 1/2019 | Shimizu et al. |
| 10,172,601 B2 | 1/2019 | Ahn |
| 10,174,933 B2 | 1/2019 | Phillips, Jr. et al. |
| 10,188,298 B2 | 1/2019 | Greenstein et al. |
| 10,213,271 B2 | 2/2019 | Duggal et al. |
| 10,219,800 B2 | 3/2019 | Tsubouchi |
| 10,220,445 B2 | 3/2019 | Vayser et al. |
| 10,226,555 B2 | 3/2019 | Vayser et al. |
| 10,238,462 B2 | 3/2019 | Wood et al. |
| D846,119 S | 4/2019 | Greeley et al. |
| 10,278,571 B2 | 5/2019 | Poormand |
| 10,292,782 B2 | 5/2019 | Haverich et al. |
| 10,292,784 B2 | 5/2019 | Duggal et al. |
| 2001/0029044 A1 | 10/2001 | Gombrich et al. |
| 2002/0022769 A1 | 2/2002 | Smith et al. |
| 2002/0038075 A1 | 3/2002 | Tsai |
| 2002/0038076 A1 | 3/2002 | Sheehan et al. |
| 2002/0055670 A1 | 5/2002 | Weiss |
| 2002/0156350 A1 | 10/2002 | Nieto |
| 2002/0165435 A1 | 11/2002 | Weiss |
| 2002/0198471 A1 | 12/2002 | Baxter-Jones et al. |
| 2003/0095781 A1 | 5/2003 | Vvillaims |
| 2003/0139673 A1 | 7/2003 | Vivenzio et al. |
| 2003/0158502 A1 | 8/2003 | Baxter-Jones et al. |
| 2003/0176772 A1 | 9/2003 | Yang |
| 2003/0187331 A1 | 10/2003 | Faludi et al. |
| 2004/0026829 A1 | 2/2004 | Van Der Weegen |
| 2004/0054260 A1 | 3/2004 | Klaassen et al. |
| 2004/0141175 A1 | 7/2004 | Baldwin et al. |
| 2004/0183482 A1 | 9/2004 | Roberts et al. |
| 2004/0184288 A1 | 9/2004 | Bettis |
| 2004/0186355 A1 | 9/2004 | Strong |
| 2005/0065496 A1 | 3/2005 | Simon et al. |
| 2005/0085699 A1 | 4/2005 | Weiss |
| 2005/0085723 A1 | 4/2005 | Huebner |
| 2005/0159649 A1 | 7/2005 | Patel |
| 2005/0192482 A1 | 9/2005 | Carpenter |
| 2005/0215858 A1 | 9/2005 | Vail, III |
| 2005/0240081 A1 | 10/2005 | Eliachar |
| 2005/0277811 A1 | 12/2005 | Richards et al. |
| 2006/0084843 A1 | 4/2006 | Sommerich et al. |
| 2006/0189847 A1* | 8/2006 | Yee ................. A61B 1/00103 600/199 |
| 2006/0200186 A1 | 9/2006 | Marchek et al. |
| 2007/0043264 A1 | 2/2007 | Gillis et al. |
| 2007/0060795 A1 | 3/2007 | Vayser et al. |
| 2007/0060938 A1 | 3/2007 | Dziadik et al. |
| 2007/0093693 A1* | 4/2007 | Geist ................. A61B 1/267 600/199 |
| 2007/0100212 A1 | 5/2007 | Pimenta et al. |
| 2007/0179342 A1* | 8/2007 | Miller ................. A61B 1/267 600/188 |
| 2007/0208226 A1 | 9/2007 | Grey et al. |
| 2007/0230164 A1 | 10/2007 | Vivenzio et al. |
| 2007/0230167 A1 | 10/2007 | McMahon et al. |
| 2007/0255110 A1 | 11/2007 | Wax et al. |
| 2007/0270866 A1 | 11/2007 | Von Jako |
| 2008/0002426 A1 | 1/2008 | Vayser et al. |
| 2008/0221569 A1 | 9/2008 | Moore et al. |
| 2008/0228038 A1 | 9/2008 | McMahon et al. |
| 2008/0269564 A1 | 10/2008 | Gelnett |
| 2008/0269565 A1 | 10/2008 | McMahon et al. |
| 2008/0278936 A1 | 11/2008 | Kurth et al. |

(56) References Cited

U.S. PATENT DOCUMENTS

| | | | |
|---|---|---|---|
| 2009/0018400 A1 | 1/2009 | Raymond et al. | |
| 2009/0069634 A1 | 3/2009 | Larkin | |
| 2009/0097236 A1 | 4/2009 | Miller et al. | |
| 2009/0112068 A1 | 4/2009 | Grey et al. | |
| 2009/0275603 A1 | 11/2009 | Krauter et al. | |
| 2009/0287192 A1 | 11/2009 | Vivenzio et al. | |
| 2009/0312610 A1 | 12/2009 | Buchok et al. | |
| 2010/0036382 A1 | 2/2010 | Bonnadier | |
| 2010/0041955 A1 | 2/2010 | Grey et al. | |
| 2010/0191062 A1 | 7/2010 | Kieffer | |
| 2010/0292533 A1 | 11/2010 | Kasahara et al. | |
| 2011/0022032 A1* | 1/2011 | Zemlok | A61B 17/07207 606/1 |
| 2011/0257650 A1* | 10/2011 | Deville | A61B 17/320092 606/45 |
| 2012/0055470 A1 | 3/2012 | Pecherer et al. | |
| 2012/0059226 A1 | 3/2012 | Funt | |
| 2012/0078060 A1 | 3/2012 | Swift | |
| 2012/0116170 A1 | 5/2012 | Vayser et al. | |
| 2012/0277780 A1* | 11/2012 | Smith | A61B 17/320092 606/169 |
| 2012/0330103 A1* | 12/2012 | Tenger | A61B 1/043 600/188 |
| 2013/0018230 A1 | 1/2013 | Su et al. | |
| 2013/0021798 A1 | 1/2013 | Chen et al. | |
| 2013/0041229 A2 | 2/2013 | Hahn et al. | |
| 2013/0046290 A1* | 2/2013 | Palmer | A61B 17/320092 606/1 |
| 2013/0092421 A1 | 4/2013 | Kajiya | |
| 2013/0197313 A1 | 8/2013 | Wan | |
| 2013/0245657 A1 | 9/2013 | Deville et al. | |
| 2013/0267786 A1 | 10/2013 | Vayser et al. | |
| 2013/0281784 A1 | 10/2013 | Ray | |
| 2013/0324801 A1 | 12/2013 | Grey et al. | |
| 2014/0088371 A1 | 3/2014 | Vayser et al. | |
| 2014/0202459 A1 | 7/2014 | Iqbal | |
| 2014/0275790 A1 | 9/2014 | Vivenzio et al. | |
| 2014/0309499 A1 | 10/2014 | Swift | |
| 2014/0316211 A1 | 10/2014 | Hermle | |
| 2014/0323800 A1 | 10/2014 | Dye | |
| 2014/0364695 A1 | 12/2014 | Nadershahi et al. | |
| 2014/0371536 A1* | 12/2014 | Miller | A61B 1/267 600/195 |
| 2015/0018625 A1 | 1/2015 | Miraki et al. | |
| 2015/0157387 A1* | 6/2015 | OuYang | A61B 18/1206 606/34 |
| 2015/0157469 A1 | 6/2015 | Prado et al. | |
| 2015/0238070 A1 | 8/2015 | Lia et al. | |
| 2015/0285382 A1 | 10/2015 | Kienreich et al. | |
| 2016/0000305 A1 | 1/2016 | Elbaz et al. | |
| 2016/0038032 A1 | 2/2016 | Dan | |
| 2016/0095506 A1 | 4/2016 | Dan et al. | |
| 2016/0100751 A1 | 4/2016 | Davis et al. | |
| 2016/0151058 A1 | 6/2016 | Ferro et al. | |
| 2016/0302657 A1 | 10/2016 | Hussey et al. | |
| 2017/0007228 A1 | 1/2017 | Costabile | |
| 2017/0020621 A1 | 1/2017 | Huldin et al. | |
| 2017/0065282 A1 | 3/2017 | Mathis et al. | |
| 2017/0079518 A1 | 3/2017 | Elbaz et al. | |
| 2017/0172404 A1 | 6/2017 | McMahon et al. | |
| 2017/0181605 A1 | 6/2017 | Lalli et al. | |
| 2017/0181607 A1 | 6/2017 | Lalli et al. | |
| 2017/0181615 A1 | 6/2017 | Vella et al. | |
| 2017/0181616 A1 | 6/2017 | Vella et al. | |
| 2017/0224206 A1 | 8/2017 | Vayser | |
| 2017/0300623 A1 | 10/2017 | Rosenblatt et al. | |
| 2017/0303903 A1 | 10/2017 | De Koning et al. | |
| 2017/0347871 A1 | 12/2017 | Wallace et al. | |
| 2017/0360423 A1 | 12/2017 | Stevenson et al. | |
| 2018/0000469 A1 | 1/2018 | Wood et al. | |
| 2018/0008137 A1* | 1/2018 | Poormand | A61B 1/07 |
| 2018/0008138 A1 | 1/2018 | Thommen et al. | |
| 2018/0008368 A1 | 1/2018 | Duggal et al. | |
| 2018/0014721 A1 | 1/2018 | Rullo et al. | |
| 2018/0014842 A1 | 1/2018 | Shener-Irmakoglu | |
| 2018/0014900 A1 | 1/2018 | Vayser et al. | |
| 2018/0021100 A1* | 1/2018 | Swift | A61B 17/02 600/245 |
| 2018/0036031 A1* | 2/2018 | Smith | A61B 17/320092 |
| 2018/0036095 A1 | 2/2018 | Vayser et al. | |
| 2018/0042596 A1 | 2/2018 | Tsubouchi | |
| 2018/0064316 A1 | 3/2018 | Charles et al. | |
| 2018/0064317 A1 | 3/2018 | Tesar | |
| 2018/0078301 A1 | 3/2018 | Vayser | |
| 2018/0116581 A1 | 5/2018 | Prasad et al. | |
| 2018/0125336 A1 | 5/2018 | Goldfarb et al. | |
| 2018/0125347 A1 | 5/2018 | Czyzewski et al. | |
| 2018/0132710 A1 | 5/2018 | Pacey et al. | |
| 2018/0132970 A1 | 5/2018 | Ritter | |
| 2018/0153391 A1 | 6/2018 | McMahon et al. | |
| 2018/0156448 A1 | 6/2018 | Phillips, Jr. et al. | |
| 2018/0206832 A1 | 7/2018 | Greeley et al. | |
| 2018/0228376 A1 | 8/2018 | Greenstein et al. | |
| 2018/0228483 A1 | 8/2018 | Duggal et al. | |
| 2018/0235444 A1 | 8/2018 | Tsai | |
| 2018/0235592 A1 | 8/2018 | Kass et al. | |
| 2018/0249902 A1 | 9/2018 | Grey et al. | |
| 2018/0263480 A1 | 9/2018 | Lalli et al. | |
| 2018/0263481 A1* | 9/2018 | Muratori | A61B 90/70 |
| 2018/0271581 A1 | 9/2018 | Ouyang et al. | |
| 2018/0280011 A1 | 10/2018 | Ferro et al. | |
| 2018/0296082 A1 | 10/2018 | Salvati et al. | |
| 2018/0317746 A1 | 11/2018 | Lalli et al. | |
| 2018/0317752 A1 | 11/2018 | Cybulski et al. | |
| 2018/0317902 A1* | 11/2018 | Green | A61B 17/0231 |
| 2018/0328572 A1 | 11/2018 | Kennedy et al. | |
| 2018/0336474 A1 | 11/2018 | Vayser et al. | |
| 2018/0344144 A1 | 12/2018 | Bouquet | |
| 2018/0353059 A1 | 12/2018 | Tesar | |
| 2018/0360301 A1 | 12/2018 | Kucklick | |
| 2019/0038273 A1 | 2/2019 | Perler et al. | |
| 2019/0049655 A1 | 2/2019 | Zagatsky et al. | |
| 2019/0076138 A1 | 3/2019 | Opperman | |
| 2019/0083079 A1 | 3/2019 | Shimizu et al. | |
| 2019/0133432 A1 | 5/2019 | Tsai | |
| 2019/0143006 A1 | 5/2019 | Vayser et al. | |
| 2019/0143414 A1 | 5/2019 | Vayser et al. | |
| 2019/0150422 A1 | 5/2019 | Welch | |
| 2019/0150725 A1 | 5/2019 | Ramanujam et al. | |
| 2019/0150739 A1 | 5/2019 | Wawro et al. | |
| 2019/0150786 A1 | 5/2019 | Vassallo et al. | |
| 2019/0167111 A1 | 6/2019 | Greenstein et al. | |
| 2019/0167378 A1 | 6/2019 | Wood et al. | |
| 2019/0190293 A1 | 6/2019 | Wawro et al. | |
| 2019/0223708 A1 | 7/2019 | Recanati et al. | |

FOREIGN PATENT DOCUMENTS

| | | |
|---|---|---|
| CN | 2516109 Y | 10/2002 |
| CN | 2629738 Y | 8/2004 |
| CN | 1565664 A | 1/2005 |
| CN | 2668152 Y | 1/2005 |
| CN | 1717195 A | 1/2006 |
| CN | 101179982 A | 5/2008 |
| CN | 201055387 Y | 5/2008 |
| CN | 203591245 U | 5/2008 |
| CN | 102415869 A | 4/2012 |
| CN | 302536685 S | 8/2013 |
| CN | 103925266 A | 7/2014 |
| CN | 203898367 U | 10/2014 |
| CN | 102573700 B | 12/2014 |
| DE | 2128855 A | 12/1972 |
| DE | 202004002963 U1 | 5/2004 |
| DE | 202005019780 U1 | 5/2006 |
| DE | 600 33 612 T2 | 12/2007 |
| EP | 0190014 A2 | 8/1986 |
| FR | 2490478 A1 | 3/1982 |
| RU | 2187972 C2 | 8/2002 |
| RU | 2308873 C2 | 10/2007 |
| WO | 9825512 A1 | 6/1998 |
| WO | 03082123 A2 | 10/2003 |
| WO | 2004064624 A1 | 8/2004 |
| WO | 2006107877 A2 | 10/2006 |

(56) References Cited

FOREIGN PATENT DOCUMENTS

| WO | 2006107878 A2 | 10/2006 |
|----|---------------|---------|
| WO | 2009137017 A2 | 11/2009 |
| WO | 2013-044151 A1 | 3/2013 |
| WO | 2014-041172 A1 | 3/2014 |
| WO | 2006121530 A2 | 11/2016 |

OTHER PUBLICATIONS

Oct. 29, 2018 Chinese Office Action, which is enclosed without an English Translation, that issued in Chinese Patent Application No. 201711159829.6.

International Search Report for International application No. PCT/US2016/016154 dated May 19, 2016 for corresponding U.S. Appl. No. 14/614,413.

International Search Report, for International application No. PCT/US2016/035508 dated Sep. 15, 2016 for corresponding U.S. Appl. No. 15/171,581.

International Search Report for International application No. PCT/US2016/036833 dated Jan. 19, 2017.

Office Action issued in U.S. Appl. No. 15/171,581.

PCT Search Report issued in PCT Application No. PCT/US2017/042617.

Nov. 1, 2017 Chinese Office Action, enclosed without an English Translation, that issued in Chinese Patent Application No. 201510543086.7.

Jul. 16, 2018 Chinese Office Action, enclosed without an English Translation, that issued in Chinese Patent Application No. 201510543086.7.

Solvey, Techinical Data Sheet, Ixef 1022 polyarylamide, Feb. 13, 2015, pp. 1-5.

http://www.makeitfrom.com/material-properties/Polyetheretheketone-PEEK, printed on Oct. 9, 2016, pp. 1-9.

International Search Report of PCT/US2018/054925, dated Oct. 9, 2018.

Supplementary European Search Report dated Apr. 24, 2019, that issued in European Patent Application No. 16804432.9.

Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.

\* cited by examiner

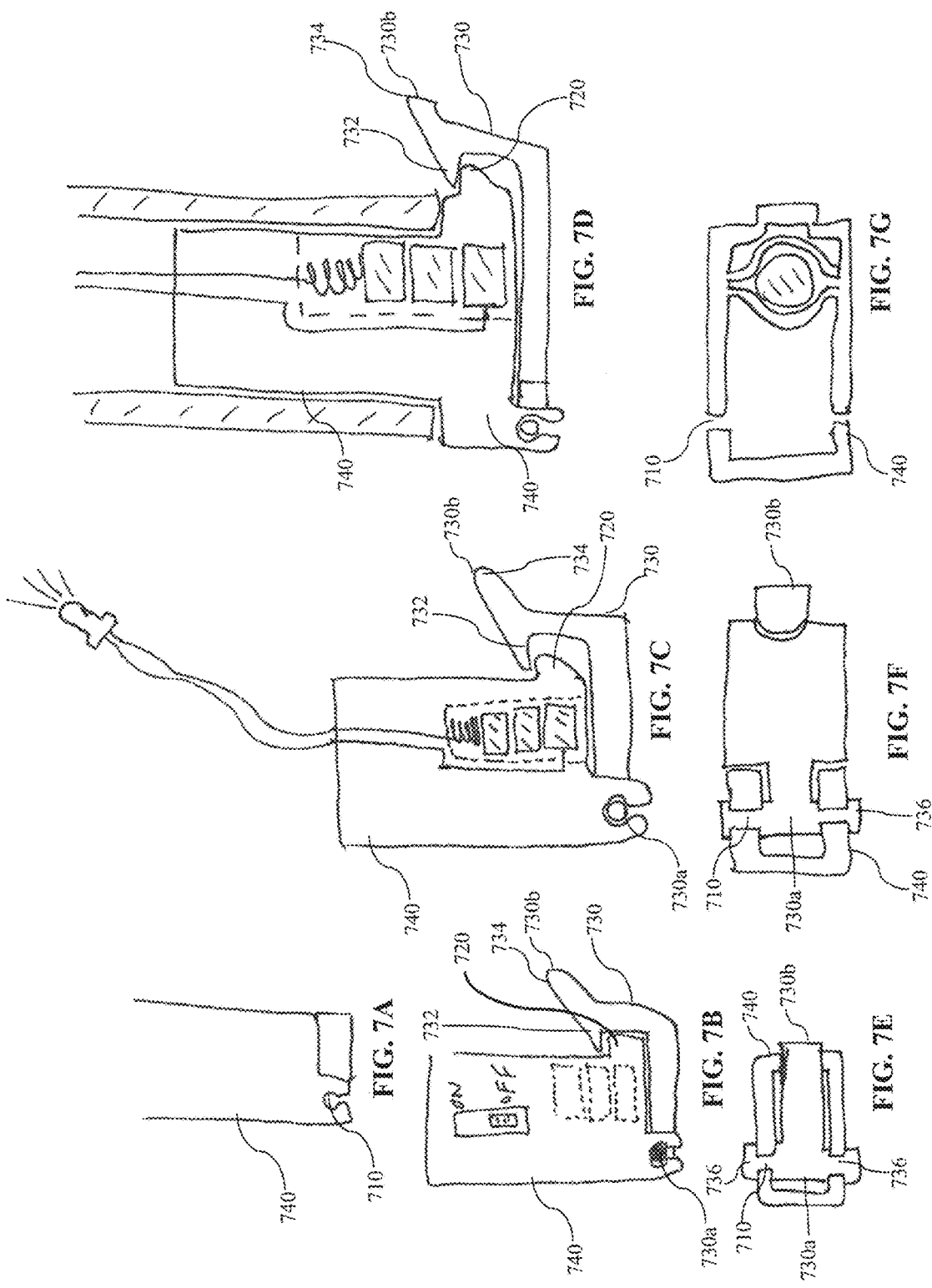

Top assembly snaps into bottom assembly.

MEDICAL DEVICES WITH BATTERY REMOVAL

BACKGROUND

The present invention relates to medical devices used for examination of a patient or during surgery, including but not limited to speculums, retractors, larygoscopes, suction devices, anoscopes, cannula and other examination and surgical devices which may use batteries, such as electrocautery devices, scalpels, sigmoidoscopes, proctoscopes, and others. For example, a speculum is a medical instrument used for dilating an opening of a body cavity for medical examinations. For instance, a two-blade speculum is commonly used in a gynecological examination. The pair of hinged blades of the speculum are configured in a "closed state" when introduced into a body cavity, for example, a patient's vagina, and the blades are articulated to an "opened state" to dilate, for example, the vaginal walls, allowing medical examiners to examine internal genital organs. In another example, a retractor is commonly used during a surgical procedure to separate the edges of a surgical incision or wound or to hold back tissues or organs to expose the area on which surgery is conducted. Varieties of other types of retractors such as laryngoscopes, nasal speculums, aural speculums, etc. are commonly used in other settings.

The conventional speculums and retractors are typically made of metals, designed to be reused subject to extensive sterilization for preventing cross contamination. However, the process of sterilizing reusable speculums and retractors proved not only to be a great nuisance but also unnecessarily costly and time-consuming. The problems exacerbate in settings such as emergency rooms, urgent care, etc. where immediate attention is desired. Thus, over time, manufacturers have developed plastic speculums and retractors made from lightweight and inexpensive materials to eliminate the above noted problems. The plastic medical and surgical devices are comparatively inexpensive and are wholly disposable after a single use.

Some retractors and speculums include illuminating means for illuminating the subject area for examination. The illuminating means generally include a light source such as a small light bulb or an LED that is operatively coupled to an external power source or to a portable power source such as a battery via simple circuitry. Generally, the illuminating means used in conjunction with disposable speculums and retractors are disposed together with the speculums and retractors. Other medical devices use a power source for powering other components of the medical device, not limited to an illumination assembly. One example of a battery-powered medical device is an electrocautery device which uses a power source for heating an electrode.

When medical speculums, retractors and other medical devices are disposed, they are generally categorized and disposed as "bio-hazardous waste" in accordance with medical waste disposal requirements, and further incinerated by an appropriate entity. However, when medical devices with the above mentioned illuminating means or other battery powered components are disposed and incinerated, the batteries contained therein comprise mercury, cadmium, zinc, nickel, chromium, lead and other heavy metals, and may cause serious pollution damage to the surrounding environment. For instance, these heavy metals can contaminate the ash released by the incinerator and pollute the air, or leach out of landfills and further pollute water sources.

Therefore, proper disposal of medical devices and recycling of batteries from disposable medical devices are desired to prevent hazardous contamination and/or pollution of the environment.

SUMMARY OF THE INVENTION

It is the objective of the present invention to provide a battery removal mechanism for a battery-operated medical device which allows easy removal of batteries without risking contamination of the batteries with biohazardous materials. It is further an objective of the present invention to provide a battery removal mechanism which can be operated by a medical professional while wearing gloves and/or other protective gear and which releases the batteries from the medical device without also removing other components of the medical device so as to avoid contamination of the batteries after removal. Another objective is to provide a battery removal mechanism for a single-use disposable battery-powered medical device so that the batteries are removed from the medical device and are disposed separately from the disposal of the medical device.

In accordance with some embodiments of the present invention, a battery-powered medical device is provided, with the medical device comprising an outer housing having an opening formed therein, a power source housed within the outer housing, the outer housing being configured to at least partially enclose the power source so as to prevent contamination of the power source with biohazardous materials, the power source being removable from the outer housing via the opening, and a cover configured to cover the opening in the outer housing and to retain the power source within the outer housing, wherein the cover is configured to be operated by a user to expose the opening in the outer housing, when the cover is operated to expose the opening, the outer housing is configured to release the power source via the opening without requiring physical contact between the user and the power source, and when the cover is operated to expose the opening, the outer housing is configured to provide a direct path for release of the power source via the opening, such path providing no contact with contaminated surfaces of the medical device.

In some embodiments, the medical device further comprises an actuator for releasing the power source from the outer housing via the opening without user contact with the power source. The actuator may be a biasing member biasing the power source in a direction of the cover when the cover covers the opening in the outer housing, and/or a band disposed partially around the power source and configured to be pulled by the user to release the power source via the opening in the outer housing.

The medical device may be a disposable single-use medical device and the removable power source comprises one or more non-rechargeable, single-use batteries. The outer housing may be configured to prevent replacement of the power source after the power source is released therefrom. In some embodiments, the outer housing comprises a handle portion having a first end and a second end, the opening in the outer housing is formed in the first end, and the power source is housed in the handle portion at a position closer to the second end than to the first end.

In certain embodiments, the outer housing is a handle portion of the medical device and the medical device further comprises an operative portion coupled to a proximal end of the handle portion. A distal end of the handle portion forms the opening in the outer housing, and the power source is biased against the cover covering the opening so that when the cover is operated to expose the opening, the removable power source is ejected from the handle portion. The medical device may further include a lock configured to retain the cover in a first position covering the opening and configured to be operated by the user to release the cover from the first position to a second position so as to expose the opening. In some embodiments, the medical device further comprises a compartment for partially enclosing the power source, with the compartment being at least partially enclosed by the handle portion and having an open side configured to communicate with the opening in the handle portion. In such embodiments, the cover is engaged with one or more of the compartment and the outer housing.

In certain embodiments, the medical device is one of a speculum, a retractor, an anoscope and a laryngoscope, and comprises an illumination assembly including at least one light source and the power source for powering the at least one light source. In such embodiments, the outer housing comprises a handle portion and at least one blade portion coupled to the handle portion, with the power source being housed in one of the handle portion and the blade portion.

In other embodiments, a battery-operated medical device is provided, with the medical device comprising: an outer housing having an opening formed therein, a power source housed within the outer housing so as to prevent contamination of the power source with biohazardous materials, and a holder configured to be movable from a first position to a second position relative to the outer housing, the holder being further configured to partially enclose the power source and to hold the power source within the outer housing when the holder is in the first position, and further configured to release the power source from the outer housing via the opening when the holder is in the second position. When the holder is in the second position, the outer housing and the holder are structured to cause the power source to be released from the outer housing while the holder remains connected to the medical device.

In some embodiments of the medical device, the holder is configured to be inhibited from being moved from the second position to the first position. In certain embodiments, when the holder is in the first position, the holder and the outer housing are configured to hold the power source between the holder and an inner wall of the outer housing, and when the holder is in the second position, the holder and the outer housing are configured to release the power source through a space between the holder and the inner wall of the outer housing. The inner wall of the outer housing may include a projection configured to abut the power source held by the holder in the first position. The holder may have a substantially C-shaped cross-section.

In some embodiments, the outer housing includes a handle portion having a proximal end and a distal end, with the opening in the outer housing being formed in the distal end of the handle portion, and the holder is configured to hold the power source within the handle portion in the first position. The holder may be configured to hold the power source in the handle portion at a position closer to the proximal end of the handle portion than to the distal end of the handle portion. In some embodiments, the medical device includes an operating member configured to be operated by a user to move the holder from the first position to the second position and wherein: the operating member is coupled to the holder and extends from the proximal end of the handle portion in the first position of the holder, and the operating member is configured to be pushed by the user into the proximal end of the handle portion so as to move the holder to the second position.

In certain embodiments, the holder comprises a compartment for partially enclosing the power source and has an open side configured to communicate with the opening in the outer housing when the compartment is in the second position. The compartment is at least partially enclosed by the outer housing. The compartment may include a sidewall configured to cover the opening in the outer housing when the compartment is in the first position, and may be configured to pivot into the second position so that the open side of the compartment is in communication with the opening in the outer housing. In some configurations, the outer housing comprises a handle portion, a blade portion and a curved portion connecting the handle portion to the blade portion, and the opening is formed in one of the handle portion, the blade portion and the curved portion. The medical device may be one of a retractor, a speculum, an anoscope and a laryngoscope, and the outer housing may comprise a handle portion and at least one blade portion extending from the handle portion. The medical device may comprise an illumination assembly that includes at least one light source and the power source for powering the at least one light source, and the opening in the outer housing may be formed in one of the handle portion and the blade portion.

In yet other embodiments, a battery-operated medical device is provided, with the medical device comprising: an outer housing having an opening formed therein, a power source housed within the outer housing so as to prevent contamination of the power source with biohazardous materials, and a holder configured to be movable from a first position to a second position relative to the outer housing, the holder being further configured to partially enclose the power source and to retain the power source within the outer housing when the holder is in the first position, and further configured to release the power source from the outer housing via the opening when the holder is in the second position, wherein at least one of the outer housing and the holder is configured to prevent replacement of the power source after the power source is released from the outer housing.

In some embodiments, the outer housing comprises a handle portion having a first end and a second end, with the opening in the outer housing being formed in the first end, and the power source being housed in the handle portion at a position closer to the second end than to the first end.

In some embodiments, the holder is configured to be inhibited from being moved from the second position to the first position. The outer housing may include a locking projection configured to engage with the holder in the second position to prevent removal of the holder from the outer housing and to inhibit moving of the holder from the second position to the first position. The medical device may include an operating member configured to be operated by a user to cause the holder to move from the first position to the second position by pushing the operating member into the outer housing.

In certain embodiments, the medical device is one of a retractor, a speculum, an anoscope and a laryngoscope, and comprises an illumination assembly including at least one light source and the power source for powering the at least one light source. The outer housing of such medical device comprises a handle portion and at least one blade portion coupled to the handle portion, with the power source being housed in one of the handle portion and the blade portion.

In other embodiments, a battery-operated medical device is provided, with the medical device comprising: an outer housing having an opening formed therein, a power source housed within the outer housing so as to prevent contamination of the power source with biohazardous materials, and a holder configured to be movable from a first position to a second position relative to the outer housing, the holder further being configured to partially enclose the power source and to hold the power source within the outer housing when the holder is in the first position, and further configured to release the power source from the outer housing via the opening when the holder is in the second position, wherein the holder is configured to be inhibited from being moved from the second position to the first position. The medical device may be one of a retractor, a speculum, an anoscope and a laryngoscope, and may include an illumination assembly including at least one light source and the power source for powering the at least one light source. The outer housing may include a handle portion and at least one blade portion coupled to the handle portion, with the power source being housed in one of the handle portion and the blade portion.

BRIEF DESCRIPTION OF THE FIGURES

The above and other features and aspects of the present invention will become more apparent upon reading the following detailed description in conjunction with the accompanying drawings, in which:

FIGS. 7A-7G shows another variation of the fourth embodiment shown in FIG. 5, including a battery holding compartment with a pivotable platform;

DETAILED DESCRIPTION

It is an object of the present invention to provide a medical device, such as a speculum, retractor, laryngoscope, anoscope, suction device, etc., which includes an illumination assembly or the like with disposable batteries and in which the batteries can be easily removed and disposed separately from the device after use. It is also an object of the present invention to provide a battery-powered medical device in which the batteries can be easily removed for separate disposal from the medical device after use, preferably without removal of other components of the medical device, and without risk of contaminating the batteries with biohazardous waste.

Figure 1:
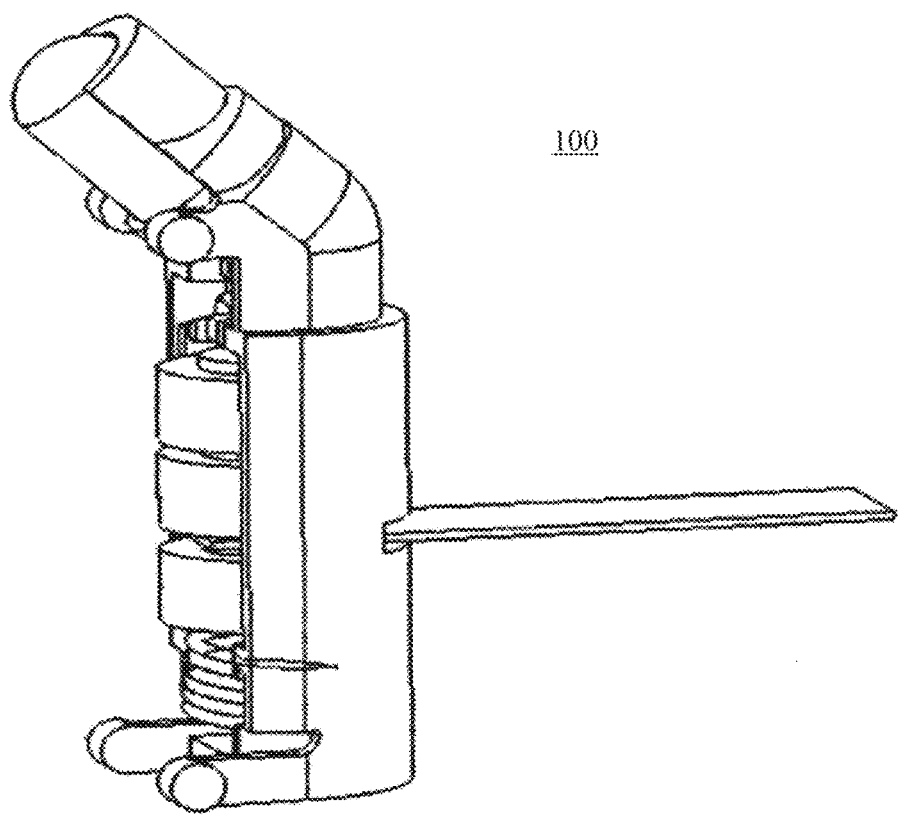
FIG. 1 shows a prior art illumination assembly for use with a medical device that retains a light source and one or more batteries.

In accordance with various embodiments of the present invention as set forth herein, an illumination assembly may be defined by a structure (e.g., a housing or a casing) that retains at least a light source and a power supply. The illumination assembly in some instances may further contain one or more conducting/non-conducting circuit elements, one or more energization/de-energization switch elements, engagement/retention elements, etc. FIG. 1 shows an exemplary prior art illumination assembly 100. Further structural and operational details regarding these types of illumination assemblies are described in at least U.S. patent application Ser. No. 14/316,787 (US Pub. No. 2014/0309499) and Ser. No. 15/178,744 (US Pub. No. 2016/0310121), both of which are incorporated herein by reference in their entireties.

As shown in FIG. 1, the housing that defines the illumination assembly 100 is a semi-enclosed (or partially enclosing) structure having at least one open side allowing access to or removal of its constituents. For example, the illumination assembly 100 is configured to fully retain and securely hold the batteries and the contained light source upon placement of the illumination assembly 100 onto a surface of a blade. Typically, the surface upon with the illumination assembly is placed (e.g., the speculum blade) provides the final, missing support for a full and complete retention.

As further shown in FIG. 1, the illustrative illumination assembly 100 is configured to attach to a speculum or retractor blade via suitable engagement means (e.g., clips, adhesives, slots and tabs, etc.). The position of attachment of the illumination assembly 100 along the blade varies from anywhere between a distal end of the blade and a proximal end of the blade, or within or extending along a curved portion (transition into handle portion) of the blade. In some devices, the illumination assembly 100 is contained entirely within the handle portion of the medical device and the light is directed to a desired area, e.g., the distal end of the speculum or retractor blade, via use of light guiding means such as a light pipe. In other devices, at least of a portion of the illumination assembly 100 is external to the device or positioned on an exterior surface thereof, e.g., on the exterior surface of the speculum or retractor blade.

The various embodiments of the present invention incorporate a similar illumination assembly but are not necessarily limited to use of the illumination assembly 100 as shown in FIG. 1. In particular, the embodiments of the present invention as described herein, as well as their respective variants, are compatible with illuminating means of any size, shape or structure. Furthermore, the embodiments of the present invention are applicable to any medical or surgical device in which one or more of the entire medical or surgical device, the illuminating means, or the batteries are configured to be discarded after use.

The embodiments of the present invention are also applicable to any medical or surgical device which is battery-operated and uses batteries for powering another component of the device, not limited to a light source. For example, the present invention may be used in an electrocautery device which uses power from batteries to heat an electrode tip. Other battery-powered medical devices may incorporate the present invention, and in particular, the battery removal mechanisms described herein.

Referring now to an exemplary embodiment of the present invention, a medical device, such as a retractor or a speculum apparatus, having an outer housing and a battery-powered assembly, such as an illumination assembly, is provided, with the battery-powered assembly having a power source, e.g., one or more batteries, at least partially enclosed by the outer housing. The outer housing of the medical device includes a handle and the medical device may further include at least one blade extending from the handle. As discussed in more details below, in some embodiments, the power source of the battery-powered assembly may be provided in the handle or may be attached to the blade. The battery-powered assembly of certain embodiments may include a bottomless battery compartment. The phrase "bottomless battery compartment" as used herein refers to a compartment, which may be part of the battery-powered assembly, such as an illumination assembly, for retaining one or more batteries in which the compartment does not completely or permanently enclose the retained batteries. It is understood that the embodiments described below may be adapted for use with other medical and surgical devices, including but not limited to laryngoscopes, anoscopes, suction devices, electrocautery devices, and any other medical or surgical devices which use portable power sources, such as batteries or power packs.

Figure 2A:
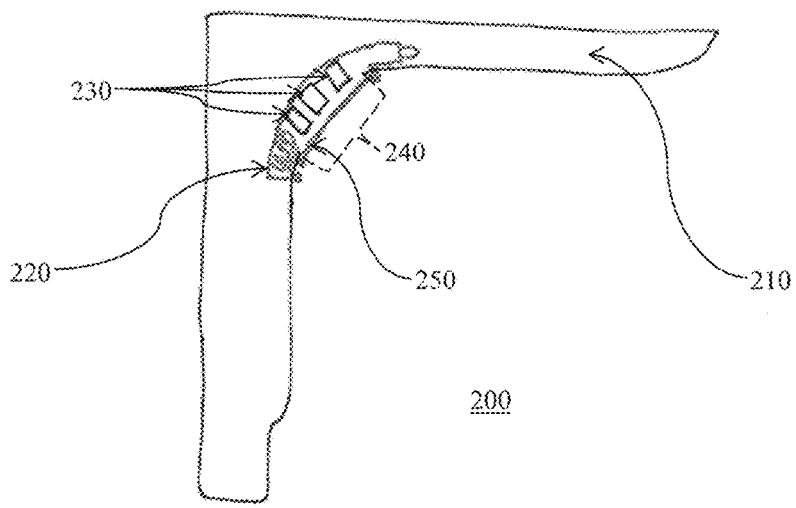
FIGS. 2A-2C show an embodiment of a battery removal mechanism of the present invention illustrating separate disposal of batteries via an opening in the speculum or retractor blade.

As shown in FIG. 2A, a speculum or retractor apparatus 200 comprises a blade 210, a handle, and an illumination assembly 220 attached to the blade 210. In this embodiment, the illumination assembly 220 includes a bottomless battery compartment that retains one or more batteries 230. As described herein, the bottomless battery compartment does not provide any retaining support for the batteries along at least one of its sides, e.g., the bottom side of the compartment that comes in contact with the surface of the blade 210.

In one version, the illumination assembly 220 is a self-contained and standalone illumination assembly in which all of the batteries are at least loosely retained within the battery compartment by a small force (e.g., adhesive, spring, electromagnetic, etc.). In this version, a small outside force (e.g., shake, turbulence, push, jerk, etc.) applied to the illumination assembly or the apparatus causes the batteries to break loose via the open side of the battery compartment. In another version, the illumination assembly 220 firmly retains the batteries within the battery compartment and requires a force exceeding a certain threshold to cause the batteries to break loose via the open side of the battery compartment. In order to avoid contaminating the batteries with biohazardous matter, it is preferred that the illumination assembly 220 is configured such that the batteries are removable from the battery compartment without coming into physical contact with the user, the user's gloves, other instruments or outside surfaces of the apparatus that may have biohazardous matter thereon.

In accordance with this embodiment, the blade 210 comprises an opening 240 that is aligned with the attachment position of the illumination assembly 220. The opening 240 of the blade 210 is typically defined by a size of a hole that is sufficiently large to allow at least the batteries 230 contained in the battery compartment to pass through and to be disposed. In one version, the opening 240 permits only the batteries to pass through and be disposed. In other versions, the opening 240 may permit the entire illumination assembly to pass through and be disposed.

Figure 2B:
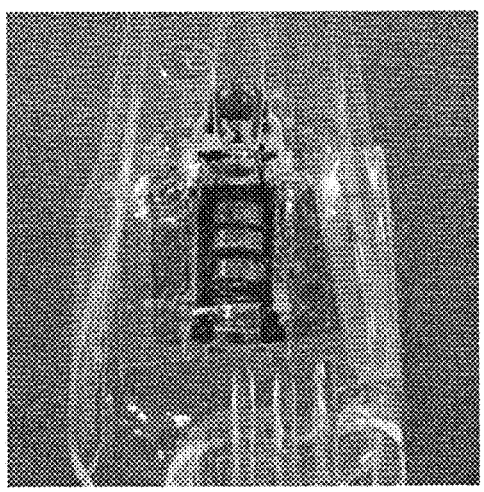

In accordance with this embodiment, the blade 210 further comprises a cover 250. The cover 250 is typically provided on the external surface of the blade and covers the opening 240. As shown in FIG. 2B, during a normal use of the apparatus 200, the opening 240 is sealed by the cover 250. The cover 250 in this state may be referred to herein as the "closed" position.

Figure 2C:
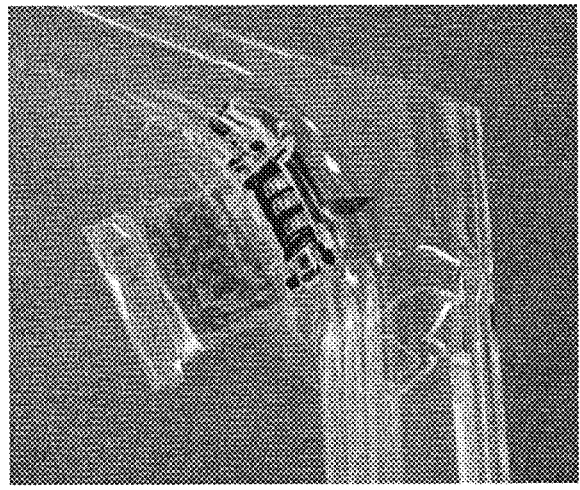

In one version, the cover 250 is provided via an adhesive that allows the cover 250 to be peeled off when disposal of the batteries is desired. For example, the cover 250 is a sticker that is placed over the opening 240 to secure the batteries 230 against its surface. The sticker may be coated so that the batteries 230 do not stick thereto but the sticker can be adhesively secured to the blade 210. In another version, the cover 250 is made of plastic material (e.g., same or similar substance as the blade). The plastic cover may be attached to the blade 210 via adhesives, hinges, latches, clips, rails, snaps, screws, or using other suitable techniques. The plastic cover may be articulated from the closed position to an "open" position by, for example, pressing onto the plastic cover, sliding the plastic cover, peeling the plastic cover, turning or rotating the plastic cover, etc. In some versions, a button may be used for releasing the cover when pressed. In a further version, the cover 250 is formed as part of the blade 210 itself. For example, the cover 250 is a hinged door that opens/closes the opening 240 or a sliding door that exposes the opening 240 for battery disposal. FIG. 2C shows an example of the cover 250 in its "open" position.

As variations to one or more of the versions of this embodiment, the illumination assembly 220, the opening 240 and the cover 250 may be positioned at the distal (front) end of the blade 210, the center of the blade 210, the proximal (rear) end of the blade 210, or within the handle, or may extend along two or more of the portions of the blade. Regardless of position, the operation of the illumination assembly with respect to the opening and the cover remains the same or substantially similar.

In accordance with this embodiment of the present invention, once the cover 250 is either removed, partially or fully peeled off, or otherwise in the open position, the user can apply a force, such as shaking, pressing or bumping the apparatus, to "pop" the batteries 230 out from their retained position. Upon such force, the batteries 230 and/or the illumination assembly 220 can be detached from the blade 210 or the handle and can be disposed separately and safely from the rest of the apparatus 200. In certain versions, no force is necessary to remove the battery(ies) and, in such versions, the batteries fall out when the cover 250 is removed, peeled or otherwise in the open position. In yet other versions, a band, ribbon or the like may be passed behind the batteries and when the cover is removed, the band or ribbon is pulled to dislodge and release the batteries. In any case, in order to avoid contaminating the batteries with biohazardous materials, the batteries are removed from the retained position without requiring the user to physically contact the batteries and without coming into contact with other portions of the apparatus or other instruments that may be contaminated by biohazardous materials. An actuator, such as band, a ribbon, a biasing member or any other type of actuator, may be used for releasing the batteries from their retained position without having the user come into contact with the batteries. In addition, the batteries are removed without making physical contact with outer or external surfaces of the apparatus which may be contaminated with biohazardous materials. In particular, the apparatus and its outer housing are configured to provide a direct path for releasing the power source with the path providing no contact with contaminated surfaces of the apparatus. This allows for proper disposal of the batteries separately from the remaining portions of the apparatus.

Another embodiment of the present invention is provided with reference to FIGS. 3A-3D. In this embodiment, a retractor or speculum apparatus 300 includes a blade 310, an illumination assembly 320 with one or more batteries 330, an opening 340 and a battery compartment 350 for holding the one or more batteries. The structure and operation of the apparatus and the illumination assembly are the same as those described in reference to FIG. 2A, and thus, further description thereof will be omitted. It is understood that although FIGS. 3A-3D show the illumination assembly 320 being disposed in the proximal end of the blade or in the area that joins the blade to the handle, in other embodiments, the illumination assembly may be provided in other areas of the blade, e.g., closer to the distal end, or in the handle portion of the apparatus in combination with a light guide or a similar device. It is also understood that this embodiment may be used with other battery-operated apparatuses, including those that do not include an illumination assembly.

In accordance with this embodiment, the battery compartment 350 houses the one or more batteries used in the illumination assembly or in another battery-operated assembly, and is inserted into the opening 340 in the apparatus 300. The battery compartment 350 includes an opening 350a at one end which allows the batteries 330 to be electrically coupled with other components, such as a light source of the illumination assembly, when the battery compartment 350 is in a closed state, and allows for removal of the batteries when the battery compartment 350 is in an open state. In the closed state, the battery compartment 350 acts as a cover for the opening wherein the outer wall of the battery compartment 350 is coextensive with the walls of the blade and/or handle.

Figure 3A:
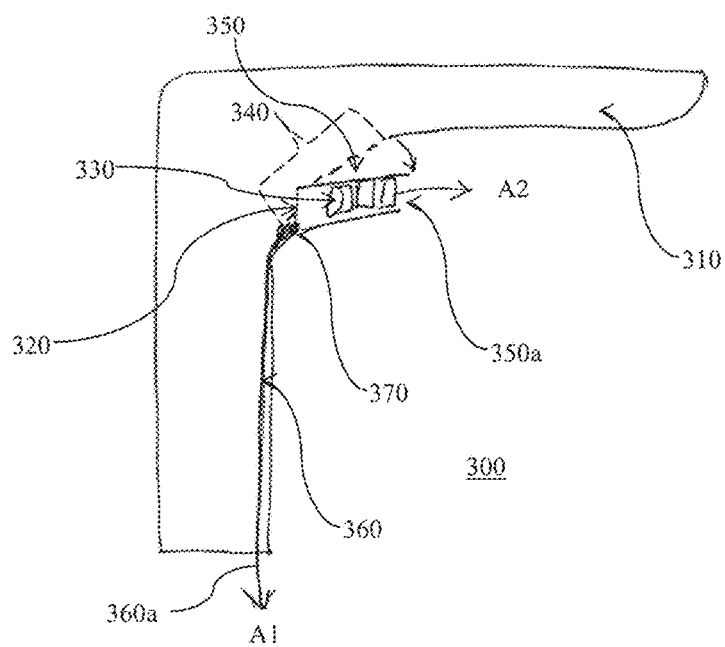
FIGS. 3A-3D show a second embodiment of a battery removal mechanism of the present invention including a release switch.
Figure 3B:
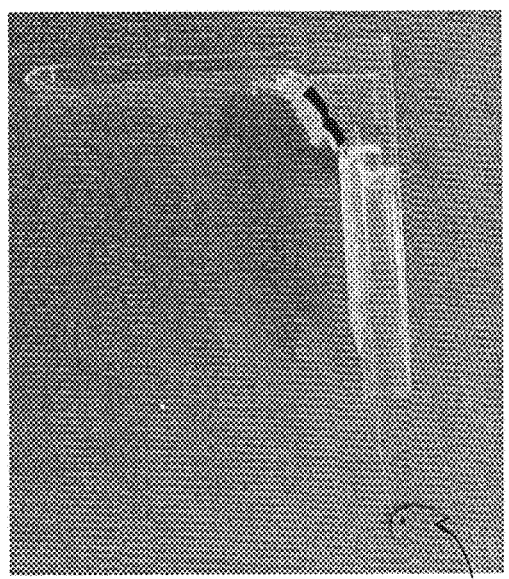
Figure 3C:
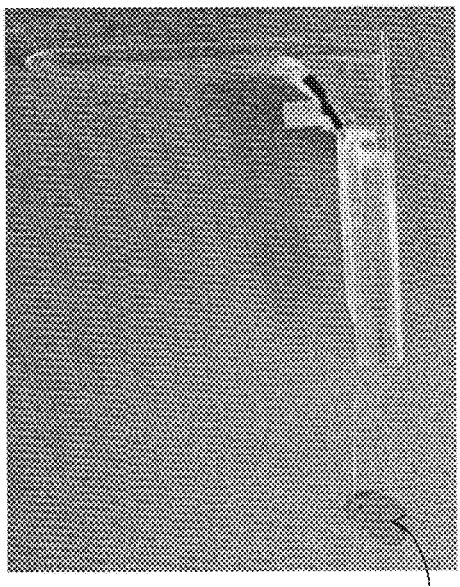

As shown in FIGS. 3A-3C, the battery compartment 350 is articulated by operating a release mechanism that includes a release tab 360 that can be moved from a first position in which the release tab 360 holds the battery compartment 350 in the closed state and a second position in which the release tab 360 allows the battery compartment 350 to drop down into an open state. In this illustrative embodiment, the release tab 360 is engaged with the battery compartment 350 at point 370, but in other embodiments, the release tab 360 may be engaged with the battery compartment 350 at other points or other types of release mechanisms to move the battery compartment from the first position to the second position may be used.

As shown in FIGS. 3B and 3C, the release tab 360 is coupled to a pull-down member 380 via a connection line 360a, which extends down through the handle portion of the apparatus. The pull-down member 380 may be inserted into or engaged with the distal end of the handle so as to form a cap or the like which can be easily removed from the handle by the user and pulled down so as to move the release tab 360 into the open state.

In operation, the user pulls on the pull-down member 380 in the direction indicated by the arrow A1, causing the release tab 360 to move from the first position to the second position so as to cause the battery compartment 350 to articulate from its closed position to its open position and to cause the batteries 330 to be disposed in the direction indicated by the arrow A2 through the opening 350a in the battery compartment. In one version, the release tab 360 opens a cover on the blade and only the batteries are disposed through the opening 350a in the battery compartment. In another variation, the battery compartment 350 may be replaced with an illumination assembly compartment holding the entire illumination assembly so that the entire illumination assembly can be disposed via the opening 340 when the illumination assembly compartment is in the open state. In another variation, the pull-down member 380 is connected directly to the battery compartment 350 or the illumination assembly compartment, and when the pull-down member 380 is pulled, the battery compartment or the illumination assembly compartment is disengaged from the closed state and the batteries or the whole illumination assembly is disposed.

FIG. 3B shows an example of a pull-down member prior to activation and FIG. 3C shows an example of the pull-down member after activation in which the battery compartment is pushed through the opening of the blade. As shown, the pull-down member may be freely hanging from the handle in some embodiments, while in other embodiments, the pull-down member may be engaged with the distal end of the cap to form an end cap or the like that is removable from the handle. In yet other embodiments, the pull-down member may be replaced by another activation mechanism, such as a switch or a pull-tab provided on the handle of the apparatus. In yet further embodiments, the activation mechanism may be disposed within the interior of the handle and is engaged or otherwise activated by placing a tool or a finger inside the handle from its open end. For example, a switch, a button, a pull-tab, a pull-down member or any other suitable mechanism may be provided on the interior of the handle or on the interior wall of the handle. In such embodiments, the activation mechanism cannot be accidentally triggered.

In the embodiment described above with respect to FIGS. 3A-3C, the battery removal mechanism uses a battery compartment or an illumination assembly compartment which is articulated between the closed position and the open position so as to release the batteries and/or the illumination assembly from the apparatus for disposal. In other embodiments, the battery removal mechanism may use a cover for covering the opening 340 and for articulating between the first position in which the cover is closed and the batteries and/or illumination assembly are retained in the apparatus and the second position in which the cover is open and the batteries and/or illumination assembly can be removed from the apparatus through the opening 340 and disposed. The same or substantially similar release mechanism is used for causing the cover to articulate between the first and second positions. In these embodiments, the batteries may be housed within a separately formed battery compartment so that when the cover is opened, the entire battery compartment with the batteries is removed. In other variations, the whole illumination assembly is housed within an illumination assembly compartment so that when the cover is opened, the illumination assembly compartment is removed, thus disposing of the entire illumination assembly. In yet other variations, the batteries are held in a partially open battery or illumination assembly compartment or case, which has an opening coextensive with the cover, so that when the cover is opened, the batteries drop down from the partially open compartment and can be disposed.

Figure 3D:
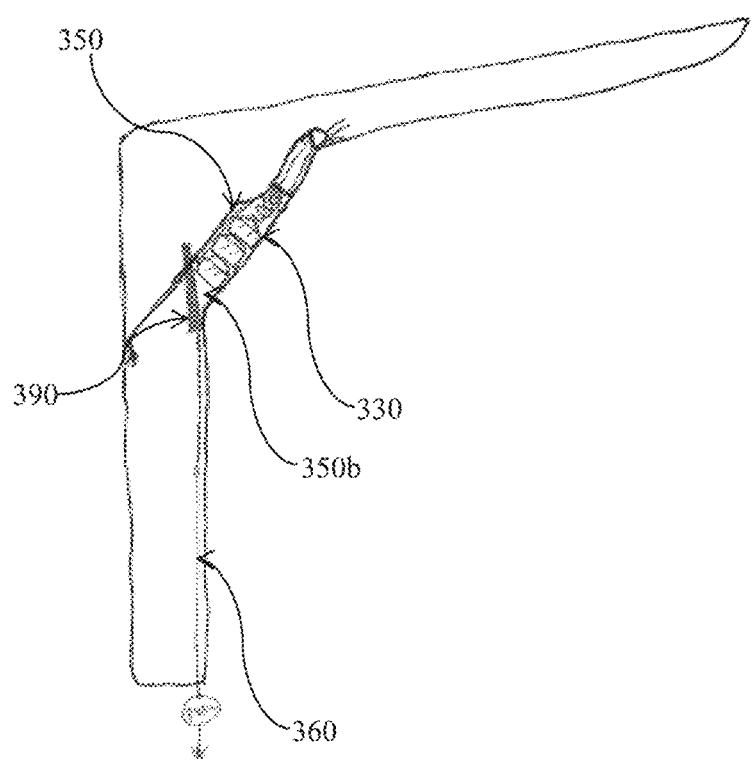

A further variation of this embodiment is shown in FIG. 3D. In this version, the battery compartment 350 includes one or more batteries 330 and an opening 350b that opens into the handle portion of the apparatus. Specifically, in this version, the battery compartment 350 is further configured with a closing tab (or a "door") 390 that holds the batteries 330 within the battery compartment 350, when the closing tab 390 is in a closed state. As shown in FIG. 3D, the batteries 330 rest on the closing tab 390 in the closed state. In the illustrated example of FIG. 3D, the batteries are disposed in the area that connects the blade to the handle portion on an angle relative to the blade and to the handle portion. However, in other variations, the batteries may be disposed in other areas of the apparatus, such as within the handle or in the blade area and the orientation of the batteries may be varied depending on the construction of the illumination assembly. For example, the battery compartment may be provided in the handle portion in a substantially vertical orientation so that the batteries are supported by the closing tab 390 in the closed state.

In FIG. 3D, for disposal of the batteries, the closing tab 390 is actuated from its closed state to an open state by pulling on the release tab 360. For example, the user can pull on the release tab 360 that hangs loose through the handle portion causing the closing tab 390 to detach from the battery compartment 350, allowing the batteries 330 to drop down through the handle portion of the speculum. In one version, the entire closing tab 390 is detached. In this version, the closing tab, once detached, is also dropped through the handle portion. In another version, the detachment of the closing tab 390 is only partial. In this version, pulling of the release tab 360 partially breaks the attachment of the closing tab 390 to the battery compartment 350 and allows the closing tab 390 to remain partially attached to the battery compartment 350 (e.g., swinging via a hinge) to release the batteries via the handle portion. In yet other versions, the closing tab may be hingedly, rotatably or slidably connected to the battery compartment 350 or to the handle portion and may be held in the closed state until the release tab 360 is pulled. In certain variations, a spring member may force the closing tab 390 into the closed state, while in other variations, the closing tab 390 may be mechanically coupled with the battery compartment 350. Pulling of the release tab 360 in these versions would cause the closing tab 390 to rotate or to slide relative to the opening in the battery compartment into the open state so that the batteries can be dropped into and through the handle portion.

In the embodiments of FIGS. 3A-3D, the apparatus is configured such that when the battery compartment is or the closing tab is moved to the open position or removed, the batteries are released through the opening in the handle or through the open end of the handle portion without requiring physical contact between the user and the batteries. In addition, the batteries are released without making physical contact with outer or external surfaces of the apparatus which may be contaminated with biohazardous materials. In addition, in these embodiments, the battery removal mechanism may configured so as to inhibit or prevent reloading or replacement of the batteries into the battery compartment. In the illustrative embodiment of FIG. 3D, after the batteries are removed and disposed, the positioning of the battery compartment does not allow easy access thereto so as to insert a new set of batteries or to reload the batteries after they are removed therefrom. In addition, in some variations, the compartment and/or the closing tab are configured so that they cannot be returned back to the closed state after being articulated into the open state. As a result, such configurations ensure that the medical device apparatus is a single-use disposable apparatus and that the medical device cannot reused.

Figure 4:
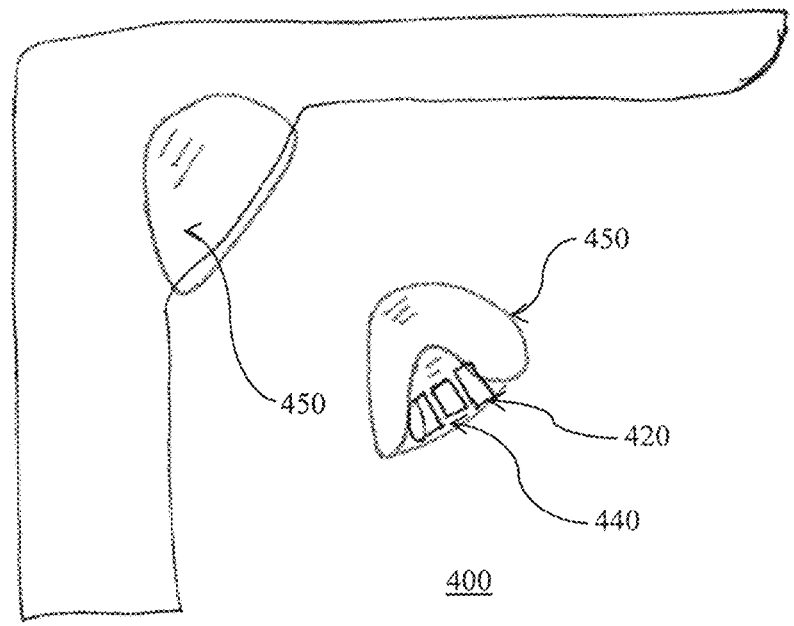
FIG. 4 shows a third embodiment of a battery removal mechanism of the present invention including a cover for the battery compartment.

A further embodiment of the present invention is shown in FIG. 4. In this embodiment, a retractor or speculum apparatus 400, similar to those described in reference to FIG. 2A, includes similar components such as the blade, the battery-operated assembly, such as an illumination assembly, with one or more batteries, an opening formed in the blade or handle, and a cover for the opening. In this embodiment, the illumination assembly 420 may include a bottomless battery compartment with an opening that corresponds to the opening in the blade or handle. Alternatively, the illumination assembly 420 may be a self-contained illumination assembly with a housing that partially houses the illumination assembly and in which the one or more batteries are at least loosely retained by the housing by a small force. In such variation, an opening in the housing for the illumination assembly corresponds at least in part with the opening in the blade or handle.

As shown in FIG. 4, the opening in the blade or handle is covered by the cover 450 which may be formed from a plastic, polymer or rubber material. The cover 450 is releasably attachable to the handle or blade or the apparatus. Any suitable fastening or attachment mechanism may be used for releasably attaching the cover to the handle or blade of the apparatus, including but not limited to providing protrusions and corresponding recesses or slots on the cover and handle or blade, using an adhesive to attach the cover to the handle or blade, or any suitable fastener. The cover 450 may be completely removable from the handle or blade of the apparatus or in certain embodiments, the cover 450 may be hingedly connected to the handle or blade so as to open and close relative to the blade or handle. In yet other embodiments, the cover 450 may be elastic and squeezable, so that the cover is fitted into the opening in the handle or blade of the apparatus and can be removed by squeezing the cover on the sides to detach it from the opening.

During operation of the apparatus, the cover 450 covers at least the one or more batteries and retains them in the illumination assembly 420. After the operation is completed and before disposing the apparatus, the cover 450 is removed to expose the batteries, and the batteries can then be removed. A small outside force such as a shake, or a jerk, applied to the apparatus, may be needed to remove the batteries. In certain embodiments, the cover 450 forms an elastic and squeezable layer around a portion of the batteries so that the cover 450 is depressible or squeezable by the user for releasing the contained batteries. Specifically, pressing on the sides of the squeezable cover 450 forces the batteries to be released through the opening 440 and to be removed simultaneously with the cover 450. The user can then dispose the batteries while holding the cover over the recycling container for the batteries. In another variation, the cover has to be articulated by sliding, rotating or the like so as to cause the batteries to be released and removed together with the cover.

In another exemplary embodiment of the present invention, an apparatus, such as a speculum, retractor, laryngoscope, anoscope, suction device, or the like, is provided in which one or more batteries for powering a light source are provided within the handle portion thereof. In accordance with this embodiment, the illumination assembly is structured such that the batteries for powering the light source are retained in the handle portion and the light source is positioned along the blade or some other component of the apparatus where illumination is needed. The batteries are connected to the light source using wires. In some versions, the illumination assembly is structured such that the batteries and the light source are both retained in the handle portion and the light is directed to the area where illumination is needed, e.g., the distal end of the blade, using a light directing means (e.g., a light pipe, prism, mirrors, etc.).

Figure 5:
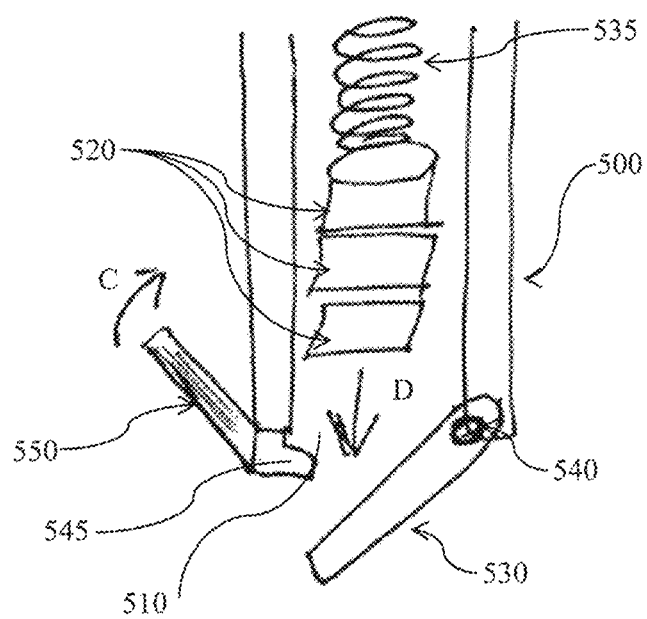
FIG. 5 shows a fourth embodiment of a battery removal mechanism of the present invention in which one or more batteries are retained in a handle portion of the medical device and the handle portion includes a releasable platform.

Referring now to the battery removal aspect, the apparatus as shown in FIG. 5 includes a handle portion 500 having an open-bottom receiving end 510 for receiving and retaining one or more batteries 520. In accordance with this embodiment, the open-bottom receiving end 510 of the handle portion 500 is covered by a platform 530 that forms an end cap or end wall of the handle portion. The platform 530 is hingedly (or rotatably) attached to the handle portion 500 via a hinge 540, and is locked in place by a tab 545 and a release switch 550. When the release switch 550 is actuated in the direction indicated by the arrow C, the tab 545 is moved away from a closed position and the platform 530 drops down and rotates via the hinge 540, which causes the batteries 520 retained in the handle portion to be disposed in the direction indicated by arrow D. Although this illustrative embodiment uses a tab 545 to hold the platform 530 in a closed position and to release the platform 530 into the open position, it is contemplated that other mechanisms may be used for retaining the platform 530 in the closed state and for releasing the platform to allow it to drop down.

In this embodiment, it should be noted that the batteries 520 are merely resting upon the platform 530 when the platform is in its "closed" position and a biasing member, such as a spring, may be used to bias the batteries 520 in a direction of the platform 530. The biasing member acts as the actuator for releasing the batteries 520 from the apparatus. As shown in FIG. 5, the spring 535 is provided above the batteries and pushes the batteries toward the platform 530. As a result, when the release switch 550 is actuated to open the platform 530, the batteries are pushed out of the handle by the force of the spring 535.

In one version, when the entire illumination assembly is positioned within the handle portion of the apparatus, all or a portion of the illumination assembly may be adhesively or mechanically attached to the handle portion. However, the batteries may be held by a bottomless battery compartment with an opening at the bottom covered by the platform 530, or as shown in FIG. 5, the handle portion may form the bottomless battery compartment that houses the batteries. In either case, when the platform 530 is opened, the batteries can drop down through the open-bottom receiving end 510 of the handle portion.

In another version, the light source of the illumination assembly is attached to the blade portion or some other portion of the apparatus where illumination is needed, and the batteries are retained in the handle portion of the apparatus, either in a separate bottomless compartment or in the handle portion itself forming the bottomless battery compartment that houses the batteries. In this version, the batteries may be held in place within the handle portion or within the separate bottomless compartment using a biasing member, an adhesive or some other retention force, but application of an external force to the apparatus causes the batteries to drop out when the platform 530 is opened. As a variation to this version, the apparatus may further comprise one or more buttons or a separate switch that causes the batteries to drop loose. Like the other embodiments, the battery removal mechanism of the embodiment of FIG. 5 can be used with other types of medical devices that include a battery-operated assembly, whether or not the battery-operated assembly is an illumination assembly or another type of assembly.

Figure 6A:
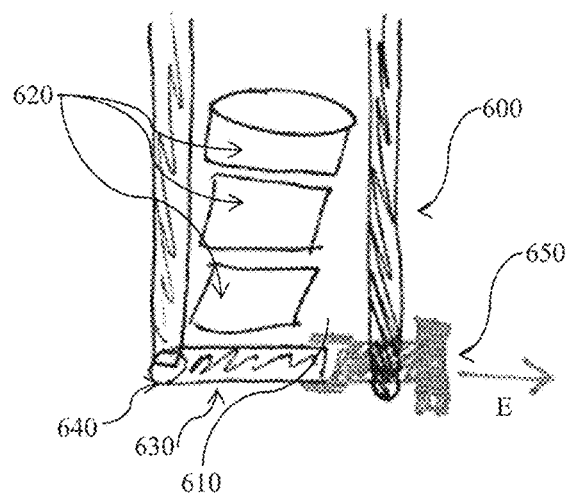
FIGS. 6A-6D show a variation of the fourth embodiment shown in FIG. 5, including a pull switch for releasing the platform.
Figure 6B:
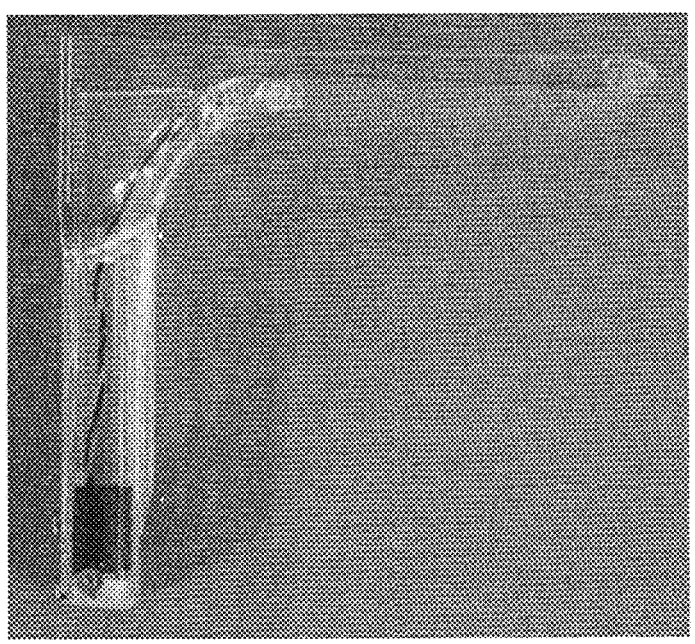
Figure 6C:
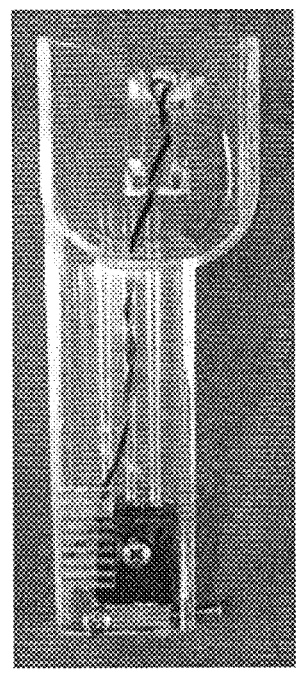

As a variation to this embodiment, the apparatus shown in FIG. 6A comprises similar components as the apparatus shown in FIG. 5, but further comprises a pull switch 650 in place of the tab 545 and the release switch 550 as described with reference to FIG. 5. In one version, the handle portion 600 includes one or more slots or holes near its open-bottom receiving end 610 through which the pull switch 650 passes. The pull switch 650, in its "closed" (or inserted) position, attaches to or otherwise secures to the platform 630. Although FIG. 6A shows the pull switch 650 holding the platform 630 at the top and bottom, in other variations, the pull switch 650 may hold only the bottom of the platform 630. In yet other variations, the pull switch 650 may be inserted into a corresponding opening in the platform 630 side edge so as to hold it in the closed position, as shown in FIG. 6C. Any other type of engagement between the pull switch 650 and the platform 630 may be used to releasably engage the pull switch 650 with the platform 630 in the closed state. Moreover, a biasing member, such as a spring member, may be used with the pull switch 650 to bias the pull switch 650 in the direction of the closed position. In this way, a predetermined pulling force on the pull switch 650 would be needed in order to disengage the pull switch 650 from the platform 630 so as to prevent accidental opening of the platform 630.

When the pull switch 650 is articulated (in direction indicated by arrow E) to its "open" (or pulled) position, the pull switch 650 separates from the platform 630 and the platform 630 drops down and rotates via the hinge 640. The batteries are disposed in the handle portion in the same manner as discussed herein in reference to FIG. 5 above, and thus, separate discussion thereof is omitted. FIGS. 6B-6C show different perspective views of the apparatus as shown and described in FIG. 6A.

Figure 6D:
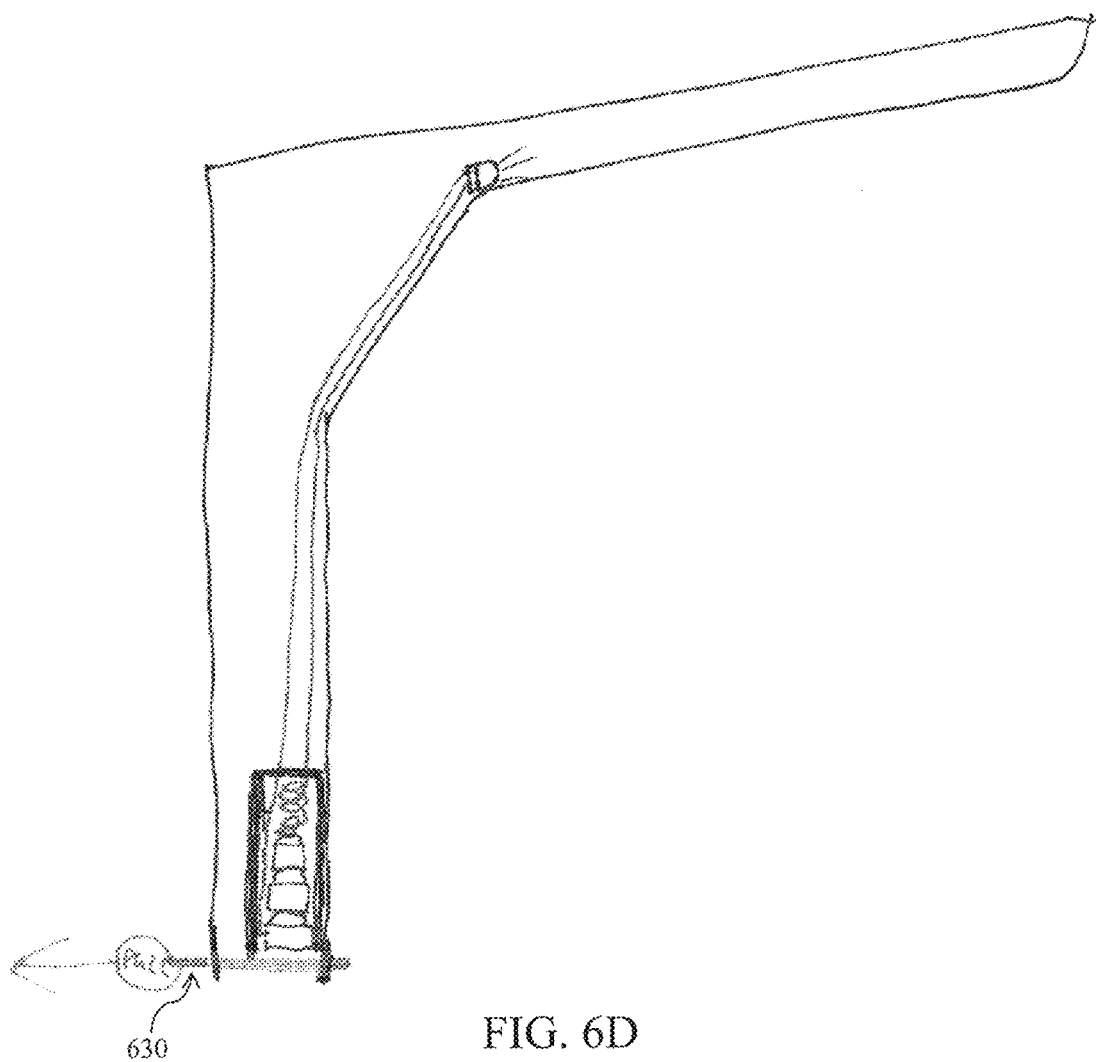

As a further variation of this embodiment, the entire platform 630 may pass through slots formed in opposing walls of the handle portion. As shown in FIG. 6D, the platform 630, having a length that traverses the entire width of the handle portion and provides a resting surface for the batteries, is provided in place of the platform-and-the-pull-switch combination shown in FIG. 6A. In this version, corresponding slots are provided in opposing walls of the lower end of the handle portion allowing the platform to be pulled in either direction. In an alternative configuration, the platform may be pulled only in one direction and may be prevented from being pulled in the other direction, e.g., by a flange or the like. Similar to the foregoing versions, once the platform 630 is removed, the batteries drop through the open end of the handle portion.

In the embodiments shown in FIGS. 5-6D, when the platform is operated to the open state or removed, the batteries are released through the open end of the handle portion without requiring physical contact between the user and the batteries. In addition, the batteries are released without making physical contact with outer surfaces of the apparatus which may be contaminated with biohazardous materials.

As further variations to embodiments as described in reference to FIGS. 5 and 6, the platform may be articulated from its closed position to open position via different methods. For example, the release switch may be an external push button or a pull tab that releases the platform. For instance, a variation that includes a battery holding compartment with a pivotable platform is shown in FIGS. 7A-7G. As shown in FIGS. 7A-7C, a battery holding compartment 740 is used for housing the batteries therein and for coupling the batteries, e.g., using wires, to the light source or to any other component of the apparatus that requires power supply. As shown in FIG. 7D, the battery compartment 740 is inserted into an open end at the bottom of the handle portion of the apparatus. Although FIGS. 7A-7C show a separate battery holding compartment 740 for housing the batteries and for releasing the batteries from the apparatus, in other embodiments, the handle portion may be configured to house the batteries directly therein and a similar pivotable platform mechanism may be used at the bottom of the handle portion as the one shown in FIGS. 7A-7C.

As shown in FIGS. 7A-7C, a bottom end of the battery holding compartment 740 is provided with an opening 710, which may be circular in cross section or any other suitable shape, and a mating portion 720, which in this illustrative example is shown as a protrusion. As more clearly shown in FIG. 7B, a pivotable platform 730 is provided, with the pivotable platform 730 having a pivoting end 730*a* and a mating end 730*b*. The pivoting end 730*a* pivotably engages with the opening 710 formed on the bottom end of the battery holding compartment 740. The mating end 730*b* and the mating portion 720 form a lock for retaining the pivotable platform 730 in a closed state when the mating end 730*b* engages with the mating portion 720 so as to lock the pivotable platform 730 relative to the battery holding compartment 740. In the illustrative embodiments shown in FIGS. 7B-7D, the mating portion 720 of the battery holding compartment 740 is formed as a protrusion extending outwardly from a sidewall of the battery holding compartment 740. In such embodiments, the mating end 730*b* of the pivotable platform 730 includes a locking tooth 732 that mates with the mating portion 720 so as to lock the pivotable portion 730 in the closed state, and further includes an operating tab 734 which can be operated by a user to release the mating between the locking tooth 732 and the mating portion 720. When the operating tab 734 is actuated by a user (e.g., by pressing), the lock between the locking tooth 732 of the pivotable platform 730 and the mating portion 720 is released and the pivotable platform 730 may be pivoted into the open state relative to a pivot point at the pivot end 730*a*. In other illustrative embodiments, the mating portion 720 may be formed as a recess so that the locking tooth 732 of the mating end 730*b* is inserted into the mating portion 720 recess in the closed state. Other configurations of the mating portion 720 and the mating end 730*b* may be used for providing a lock (a locking mechanism) for locking the pivotable platform 730 to the battery holding compartment 740.

As further shown in FIG. 7C, the pivotable platform 730 in its "closed" position provides a surface on which one or more batteries rest within the battery holding compartment 740. The batteries are electrically connected to a distantly positioned light source via electrical wires extending through the handle portion. In other medical devices, the batteries are electrically connected to other battery-powered components of a battery-operated assembly provided in the device. For disposal of the speculum and/or the batteries, the pivotable platform 730 is released from engagement with the mating portion 720 via an external force applied to the operating tab 734 at the mating end 730*b*. The pivotable platform 730 then pivots via the pivoting end 730*a* and permits the batteries to drop through the open bottom of the speculum handle portion. As shown in FIGS. 7C-7D, a spring or another type of biasing member (i.e., an actuator) may be provided at the top of the batteries so as to bias the batteries in the direction of the opening in the battery holding compartment, i.e., in the direction of the pivotable platform 730. These embodiments, when the platform is pivoted to the open position, the batteries are released from the battery holding compartment without requiring physical contact between the user and the batteries. In addition, the batteries are released without making physical contact with outer surfaces of the apparatus which may be contaminated with biohazardous materials.

In the embodiment described above and shown in FIGS. 7B-7D, the pivotable platform 730 is configured together with a battery holding compartment 740 as a standalone structure. In such version, as shown in FIG. 7D, the battery holding compartment is sized and/or shaped such that it is insertable (or fittable) into the hollow end of the handle portion. In this version, the mating portion is included on the battery compartment 740. When the standalone structure is received a certain length within the hollow end of the handle portion, the user can actuate, by operating the operating tab 734, the mating end 730*b* of the pivotable platform 730 to pivot the platform to its open position. In another version, the mating portion may be provided on the handle portion instead of on the battery compartment 740.

FIGS. 7E-7G show respective bottom views of the foregoing examples of FIGS. 7B-7D. As shown in FIGS. 7E and 7G, the battery holding compartment 740 includes openings or recesses 710 in opposing walls thereof at the lower end. In FIG. 7E, the pivotable platform 730 includes a pair of legs or shafts 736 projecting from the sides of the platform at or near the pivoting end 730*a*. The legs 736 are inserted into the corresponding openings or recesses 710 in the walls of the battery holding compartment 740. In the illustrative example shown, the openings or recesses 710 have a smaller cross-section than the thickness of the legs 736 at an initial point of insertion, with the cross-section increasing to accommodate the thickness of the legs. In this configuration, the legs 736 of the platform 730 snap into the openings or recesses 710, and can be prevented from disengaging from the openings or recesses 710. As shown in FIG. 7E, the body of the platform may be narrower than the opening in the battery holding compartment 740 as long as the platform 730 can retain the batteries within the battery holding compartment 740 and prevent contamination of the batteries with biohazardous materials. In other variations, the body of the platform 730 is the same width or wider than the opening in the battery holding compartment 740. A platform 730 with a greater width than the opening in the battery holding compartment 740 may further protect the batteries from contamination with biohazardous materials, particularly in medical devices in which the handle may be exposed to biohazardous materials during use.

Figure 8A:
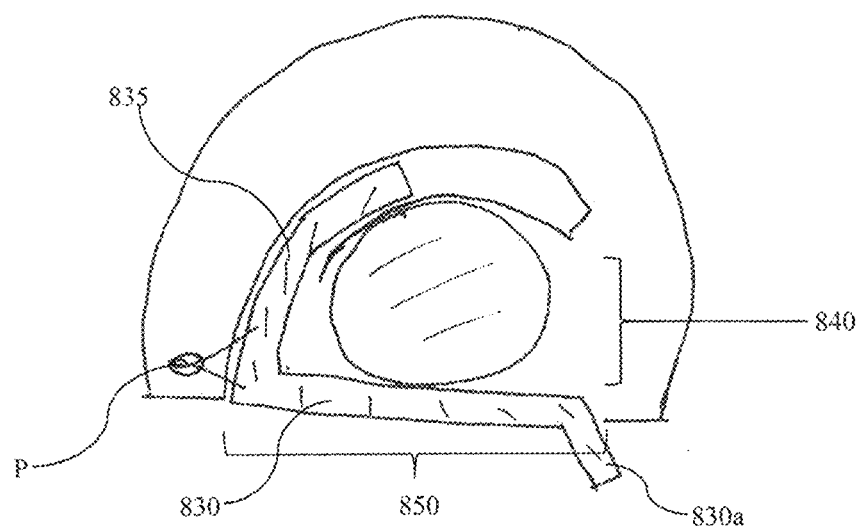
FIGS. 8A-8B shows a fifth embodiment of a battery removal mechanism of the invention, including a rotatable ejection mechanism.
Figure 8B:
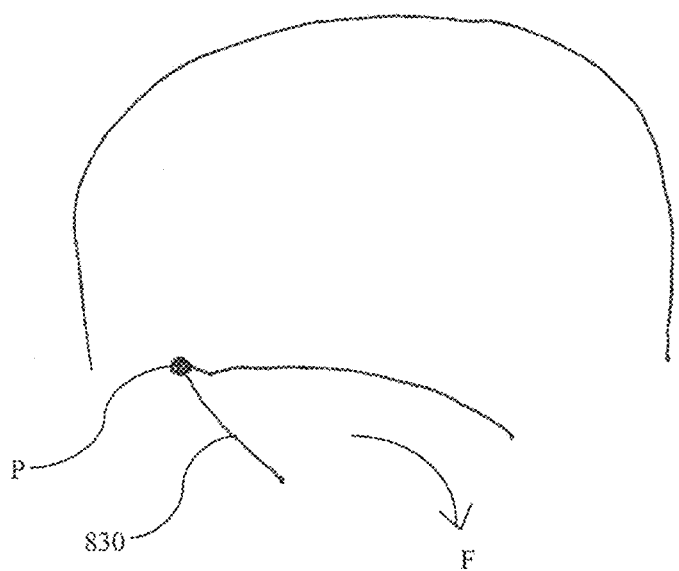

Another embodiment of a battery removal mechanism for removing and disposing batteries from a speculum or retractor apparatus is shown in FIGS. 8A-8B. FIGS. 8A-8B show a cross-sectional view looking axially down a handle portion having a battery ejection mechanism for removing batteries disposed within the handle portion through an opening 850 formed in a sidewall of the handle portion. The ejection mechanism includes a door 830 that covers the opening 850 in the handle portion and includes with an ejection lever 835 extending partially around the batteries housed within the handle portion. The door 830 is pivotable around a pivot point P between a closed state, shown in FIG. 8A, and an open state shown in FIG. 8B. The door 830 also includes an operation tab 830a which can be operated (e.g., by pressing) by a user to open the door 830 so as to move it from the closed state to the open state. When the door 830 is opened, the ejection lever 835, which moves together with the door 830, pushes the batteries through the opening 850 in the handle, thereby ejecting the batteries from the apparatus.

More specifically, as shown in FIG. 8A, the door 830 is in its closed state. The door 830 and the ejection lever 835 are structured and/or shaped in a manner such that the one or more batteries can be released (or pulled) through an side opening 840 formed between the door 830 and the ejection lever 835 using a small force or without using any force. In one version, the door 830 and the ejection lever 835 may be made of elastic material and the size of the side opening 840 is smaller than the diameter of the retained batteries. In this version, a small force, such as a tap on the handle or a shake, would be required to release the batteries when the door 830 is in the open state. In another version, the door 830 and the ejection lever 835 are made from plastic or polymer materials and the size of the side opening 840 is the same or larger than the diameter of the batteries. In this version, no force is needed to release the batteries when the door is in the open state. In any case, when the door is operated to the open state, the power source is released via the opening 840 without requiring physical contact between the user and the power source. In addition, the power source is released without making physical contact with outer surfaces of the apparatus which may be contaminated with biohazardous materials.

When the operation tab 830b on the door is operated by a user, the door 830 and the ejection lever 835 rotate around the pivot point P, and as they rotate, the side opening 840 formed between the door and the ejection lever is exposed through the side opening 850 in the handle portion, and the batteries are pulled/pushed forward and out the opening 850 in the handle portion. As discussed above, the batteries may be released through the side opening 840 with no or little force and without requiring the user to come in physical contact with the batteries. FIG. 8B illustrates the batteries being released in the direction indicated by arrow "F." As a variation to the embodiment shown in FIGS. 8A and 8B, a column-shaped structure (hereinafter "structure") with a hollow center and sidewalls for retaining and partially enclosing one or more batteries may be provided in the handle portion. The structure may have a platform for supporting the one or more batteries thereon, with the platform being connected to the sidewalls so as to be movable together with the rest of the structure. The structure is sized to be insertable and pivotable through the opening 850 in the handle portion of the apparatus relative to the pivot point P. The cross-section of the sidewalls of the structure is substantially the same or similar to that of the door and ejection lever shown in FIG. 8A. Similar to the door and the ejection lever shown in FIG. 8A, the structure includes a circumferential sidewall that covers the opening 850 in the handle portion of the apparatus and extends around the one or more batteries but does not completely encircle the batteries. For example, the circumferential sidewall includes an opening that allows the retained batteries to be released therethrough when the structure is rotated from the closed state to the open state. The rotation of the structure about the pivot point and the release mechanism for the batteries in the structure are similar to those described with respect to FIGS. 8A and 8B.

Further variations to the embodiments described in reference to FIGS. 5-8 are also contemplated. For example, the release switch shown in FIG. 6A may be an external push button that releases the platform. As another example, the platform shown in FIG. 6D may include further components that can be pushed or pulled to assist in articulation of the platform to its open position.

Figure 9A:
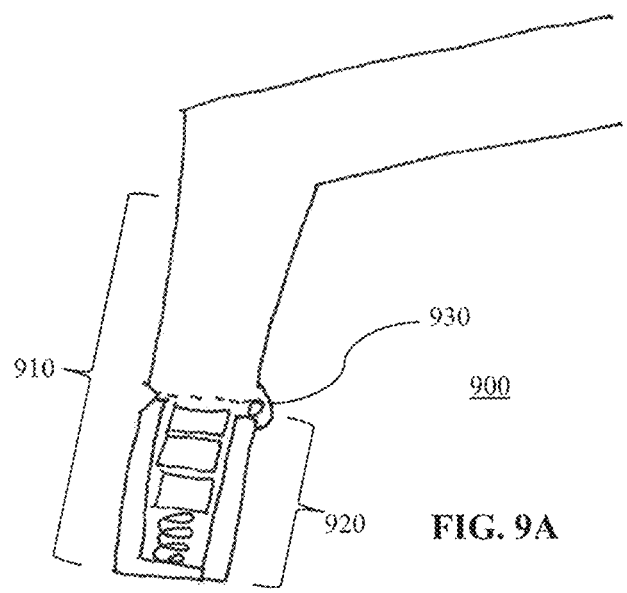
FIGS. 9A-9B shows yet a sixth embodiment of a battery removal mechanism of the present invention in which batteries are retained in the handle portion and part of the handle portion retaining the batteries are breakable from the remainder of the handle portion.
Figure 9B:
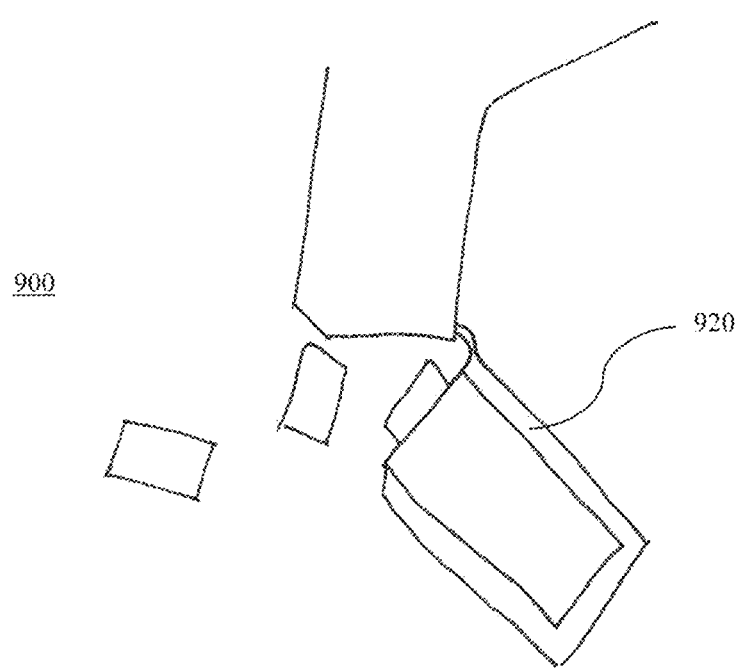

In yet another embodiment of the present invention, the handle portion of the apparatus is configured such that at least a portion thereof is breakable or detachable from the rest of the handle portion. As shown in FIG. 9A, the apparatus 900 includes a handle portion 910 in which a lower end portion 920 is breakable or detachable from the remaining portion of the handle portion 910. In accordance with this embodiment of the present invention, one or more batteries are retained within the lower end portion 920 that is breakable or detachable from the rest of the handle portion 910. In one embodiment, the breakable lower end portion 920 completely detaches from the rest of the handle portion 910. In another version, a hinge 930 is provided between the breakable lower end portion 920 and the rest of the handle portion 910 such that when the breakable lower end portion 920 is articulated to be "broken off" or detached from the handle portion 910, the breakable lower end portion 920 hinges via the hinge 930 and the one or more batteries retained therein are released and can be disposed. FIG. 9B illustrates disposal of the batteries when the breakable lower end portion 920 is separated from the rest of the handle portion of the apparatus and hinges via the hinge 930. Actuation of the breakable lower end portion 920 as described herein may be enabled using a variety of different methods such as manual force (pressing, twisting, pulling, etc.), a pull switch, a push button, or other similar techniques. The breakable lower end portion 920 cannot be reconnected and returned to the previous state of being attached to the upper portion of the handle. As a result, reloading or replacement of the batteries for additional use of the apparatus, after the batteries are removed and disposed, is inhibited. This facilitates disposability and one-time use of the apparatus and prevents reuse of the apparatus. In addition, after the breakable lower end portion 920 is separated, the batteries are released through the open end of the handle portion without requiring physical contact between the user and the batteries, and without making physical contact with outer surfaces of the apparatus which may be contaminated with biohazardous materials.

The embodiments as described herein are intended to present a concept of separate disposal for batteries used in a medical device. In certain embodiments, a platform placed at the bottom end of the handle portion of the medical device is opened in one of many different ways to allow the batteries to be disposed separately and quickly and without requiring physical contact between the user and the batteries and without the batteries making physical contact with outer surfaces of the apparatus which may be contaminated. In certain other embodiments, the blade or handle of the medical device includes an opening through which the batteries held in a bottomless battery compartment of an illumination assembly are disposed separately and quickly. In certain other embodiments, portions of the medical device that retains the batteries are detached completely or partially from the medical device itself. When the portions of the medical device are partially detached, only the batteries can be removed and disposed without requiring further separation of the batteries from the completely detached components. This allows for easier removal and separate disposal of the batteries. In addition, in certain embodiments described above, reloading or replacement of the batteries after the batteries are removed from the apparatus is inhibited, thus providing a truly disposable apparatus that cannot be reused. This can be accomplished by positioning the batteries in a location within the apparatus that is not easily accessible to the user and/or by preventing the cover or battery compartment from returning to its original, closed position. As discussed above, separate disposal of batteries solves the problems of hazardous contamination and/or pollution of the environment. Furthermore, since the batteries are removed from a medical device that includes an illumination assembly at the time of disposal, users need not worry about throwing out lit up medical devices in the trash.

FIGS. 10A-10G show another embodiment of a medical device, and in this illustrative embodiment, a speculum 1000, which includes a battery removal mechanism that uses a battery compartment or holder 1060 (also referred to as a "battery sled") provided in a handle 1034 of the speculum 1000. The battery compartment 1060 holds batteries 1074 within the handle 1034 in a retained state, which is the operating state of the speculum, and allows the batteries 1074 to be released and disposed through an opening in a bottom of the handle in an ejected state. Although FIGS. 10A-10G show the battery removal mechanism provided in the speculum, the same or similar battery removal mechanism may be provided in another type of medical device that uses batteries, including but not limited to a retractor, an anoscope, a laryngoscope, a nasal speculum, an otoscope, an aural speculum, a suction device, a cannula or any other examination and/or surgical device which uses one or more batteries. As discussed above, the medical devices in which the battery removal mechanism may be used are not limited to medical devices with an illumination assembly and the battery removal mechanism may be used in any battery-operated medical device with a battery operated assembly, such as an electrocautery device.

Figures 10A, 10B:
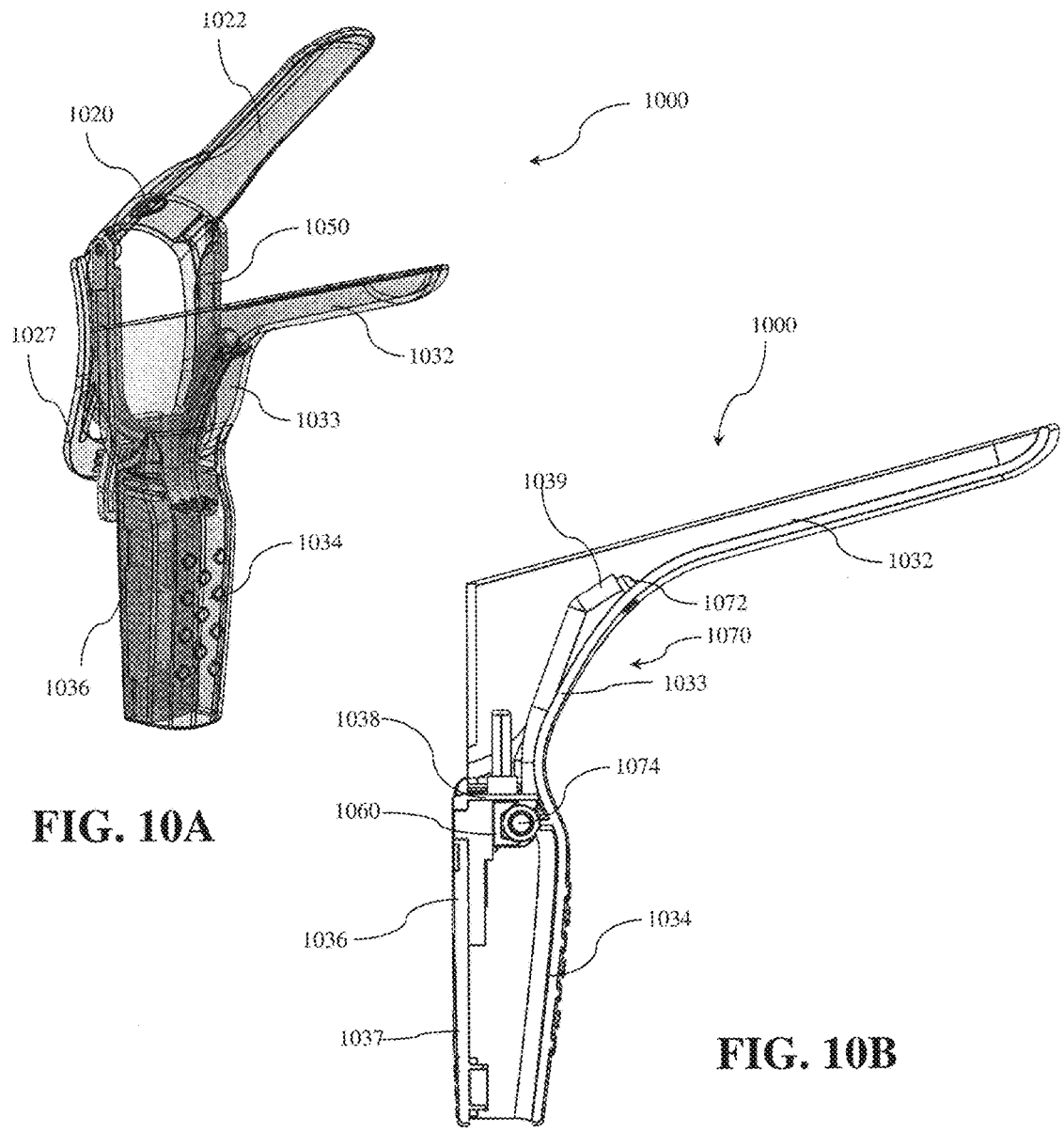
FIGS. 10A-10B show a medical device with a seventh embodiment of a battery removal mechanism of the present invention.

FIGS. 10A-10B show a general assembled configuration of the speculum 1000 of this embodiment. The speculum 1000 includes an upper member 1020 comprising an upper blade 1022 and an operating mechanism 1027, a lower member 1030 comprising a lower blade 1032, a handle 1034 and a rear faceplate assembly 1036 that engages with the handle 1034, and a linear support member 1050 which hingedly engages with the upper member 1020 for angular adjustment between the upper and lower blades, and slidably engages with the rear faceplate assembly 1036 for vertical adjustment between the upper and lower blades. When the battery removal mechanism is used with a different type of a medical device, the general configuration of the medical device would be different. For example, a retractor, laryngoscope or anoscope medical device would typically include a handle and a blade and in some configurations, may include a rear faceplate assembly similar to the rear faceplate assembly 1036 of FIGS. 10A-10B that engages with the handle. The general configurations of other types of medical devices may be adjusted as needed for the functioning of the medical device.

The speculum 1000 includes an illumination assembly 1070 comprising at least one light source 1072, such as an LED or similar light emitting device, one or more batteries 1074 and wires (not shown) electrically connecting the light source 1072 with the one or more batteries. The illumination assembly may also include an activation device (not shown), which can be in a form of a pull tab, a button, a switch, a motion detector or the like, for activating the light source 1072 from an OFF state to an ON state and vice versa.

Figures 11A, 11B:
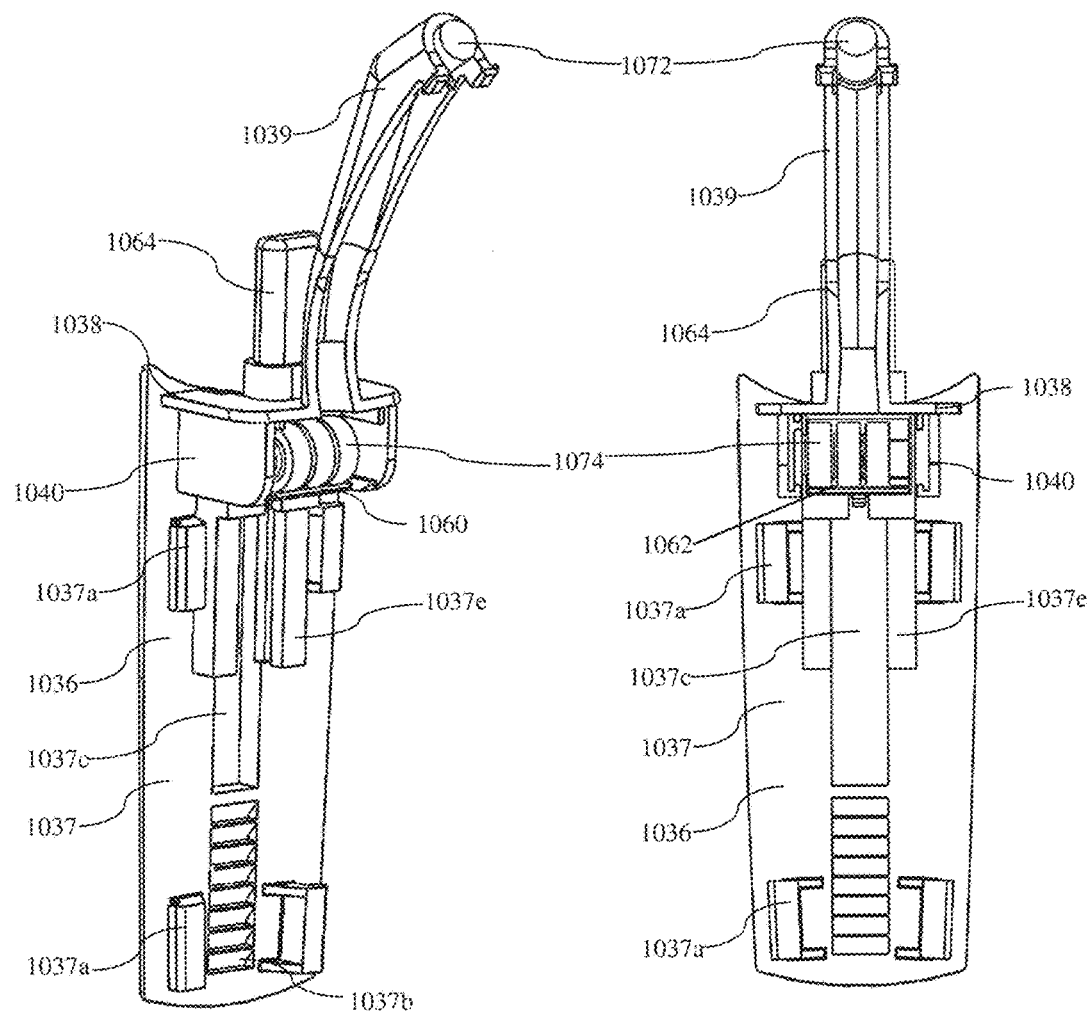
FIGS. 11A-11B show the seventh embodiment of the battery removal mechanism of FIGS. 10A-10B with a battery compartment in a retained state.

As shown in FIG. 10B and shown in more detail in FIGS. 11A and 11B, the rear face plate assembly 1036 includes a rear faceplate 1037 that engages with sidewalls of the handle 1034 and forms a rear wall of the handle 1034. The rear faceplate assembly 1036 also includes a shelf portion 1038 which extends from an upper end of the rear faceplate 1037 and an illumination assembly cover 1039 which extends from the shelf portion 1038. The illumination assembly cover 1039 extends along an inner surface of a front wall of the handle 1034 and along a curved portion 1033 that connects the handle and the lower blade 1032. The illumination assembly cover 1039 is open on the side that abuts the inner surface of the handle 1034 and the curved portion 1033, and encloses the wires connecting the batteries 1074 and the light source 1072. In this illustrative embodiment, the illumination assembly cover 1039 also partially encloses the light source 1072, which protrudes from an end of the illumination assembly cover 1039. In the present illustrative embodiment, the illumination assembly cover 1039 is engaged with the curved portion 1033 using tabs formed on the illumination assembly cover that engage with corresponding slots formed in the curved portion 1033. However, in other embodiments, the illumination assembly cover 1039 may engage with the handle 1034 and/or with the lower blade 1032.

In the embodiment shown in FIGS. 10A-10B, the illumination assembly 1070 is configured so that the light source 1072 is positioned adjacent the curved portion 1033 of the lower member. However, in other embodiments, the light source 1072 may be positioned closer to the lower blade 1032 or adjacent the lower blade 1032, at any location along the length of the lower blade 1032. In some embodiments, the illumination assembly cover 1039 may extend further than in the embodiments shown in FIGS. 10A-10B. For example, the illumination assembly cover 1039 may extend along a portion of the lower blade 1032. In some embodiments, the illumination assembly cover 1039 may also function as a smoke evacuation channel and may extend along the lower blade 1032 toward the distal end of the blade 1032.

FIGS. 11A-11D and 12A-12C show the rear faceplate assembly 1036 together with the battery compartment 1060 and the illumination assembly 1070. In FIGS. 11A-11D, the battery compartment 2060 is in the retained or operating state, while in FIGS. 12A-12C, the battery compartment is in the ejected state. In addition, FIG. 13 shows the rear face plate assembly 1036 without the battery compartment.

As shown in FIGS. 11A-11B, 12A and 13, the rear faceplate 1037 includes a plurality of engagement portions 1037a protruding from an inner surface thereof and configured to engage with corresponding protrusions formed on the inner side of the handle sidewalls. In certain embodiments, the protruding engagement portions 1037a may engage with a channel or one or more recesses formed in each of the handle sidewalls. In the illustrative embodiment of the speculum in FIGS. 10-14, the inner surface of the rear faceplate 1037 includes a plurality of stop tabs 1037b for engagement with a lock tooth of the linear support member for vertical adjustment. In other embodiments of the speculum, the rear faceplate 1037 may include a plurality of stop tabs on an opposing, outer surface thereof. As also shown in FIGS. 11A-11B, the rear faceplate 1037 includes a through recess 1037c extending along its length which is used for sliding the linear adjustment member therein so as to provide for vertical adjustment. In the embodiments of FIGS. 10-14, the rear faceplate also includes rail portions 1037e protruding from the inner surface thereof and extending on each side of the through opening. The rail portions 1037e guide the linear support member 1050 when it is inserted into the through recess 1037c. These features of the vertical adjustment mechanism may be omitted when the battery removal mechanism is employed in a different type of medical device, such as a retractor, a laryngoscope, an anoscope, etc.

The battery compartment 1060 comprises a housing 1062 for holding the batteries 1074 in the retained state, and an operating member 1064, which can be operated by a user to cause the housing 1062 to move from the retained state to the ejected state. In the present illustrative embodiment, the operating member 1064 is a button protruding from the top surface of the housing and in an assembled state of the speculum, extending from a proximal end of the handle. When the battery compartment 1060 is assembled with the rear faceplate assembly 1036, the operating member 1064 passes through an opening formed in the shelf 1038 of the rear faceplate assembly 1036. The shelf has a pair of sidewalls 1040 extending from a lower surface of the shelf and surrounding the batteries 1074 held by the battery compartment 1060 in the retained state. The sidewalls 1040, together with the housing 1062 of the battery compartment 1060 hold the batteries 1074 in place and prevent dislodgement of the batteries. One or both of the sidewalls 1040 may include coupling elements attached thereto for electrically coupling the batteries 1074 to the wires. In addition, one or more biasing members, e.g., a spring, may be used to hold the batteries 1074 in place between the sidewalls 1040.

Figure 11C:
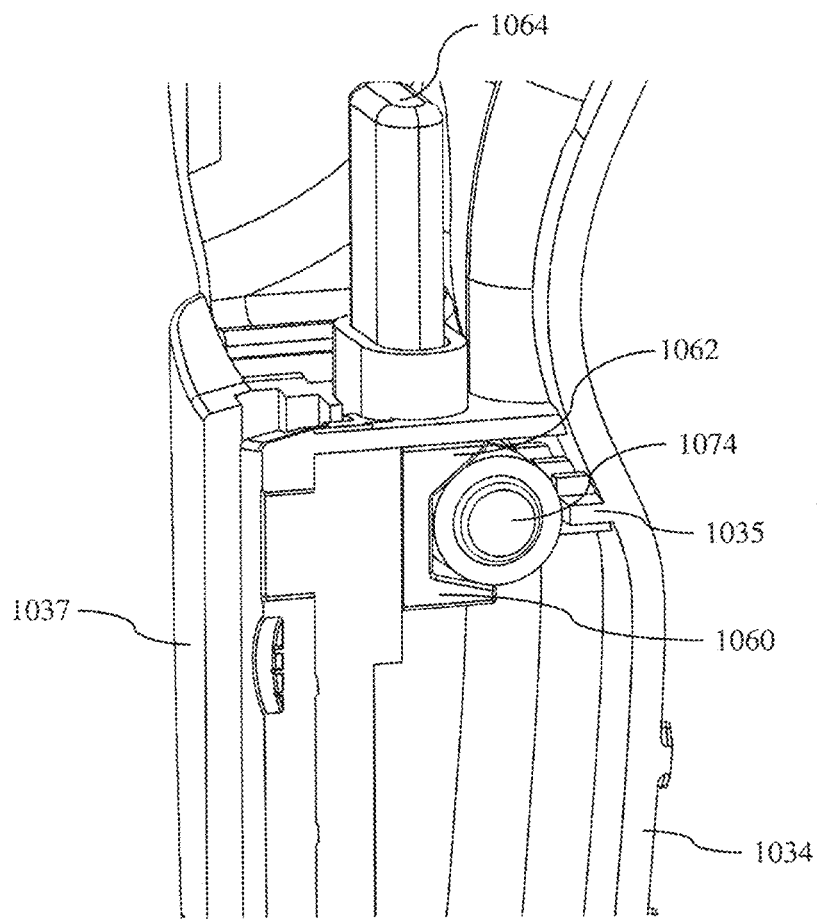
FIGS. 11C and 11D show a cross-sectional view of the medical device with the seventh embodiment of the present invention.
Figure 11D:
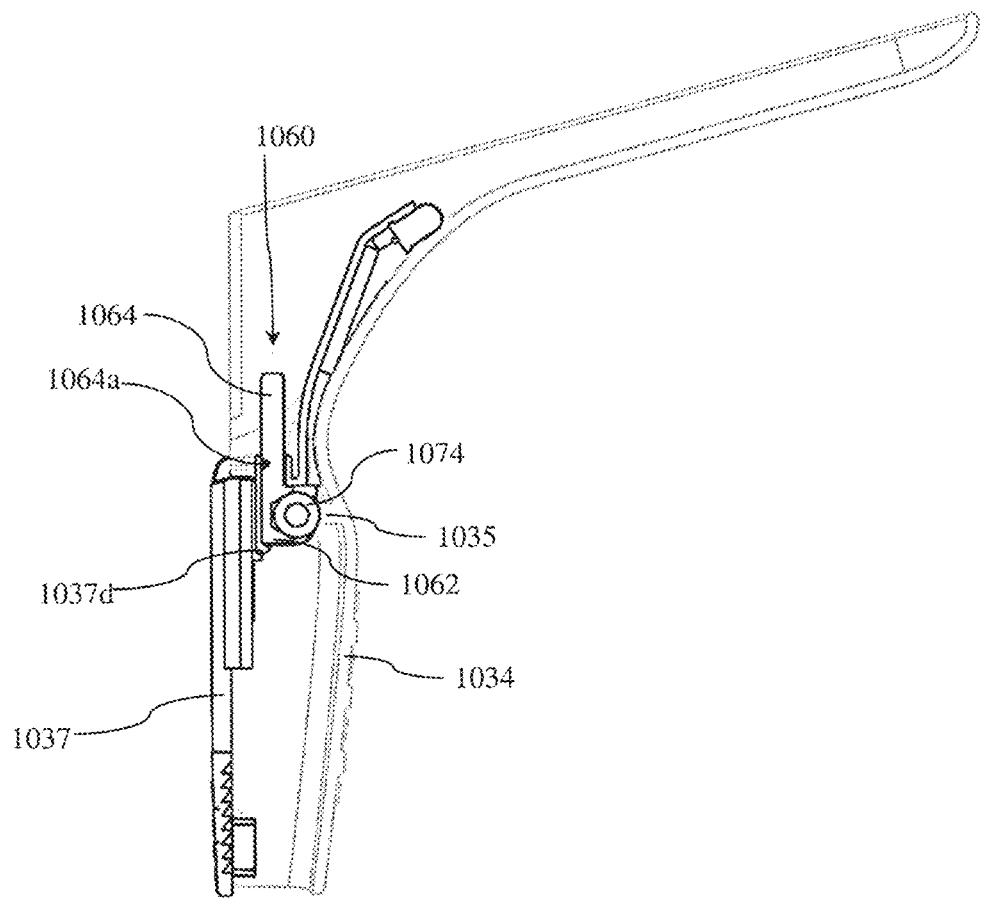

FIGS. 11C-11D show a cross-section of the speculum in which battery compartment 1060 is engaged with the rear face plate assembly 1036 in the retained state. As shown in the close-up view of FIG. 11C, the housing 1062 is a C-shaped housing which has an open side and holds the batteries 1074 against a projection 1035 formed on an inner front surface of the handle. Thus, in the retained state, the batteries 1074 are held in the C-shaped housing 1062 and are supported from the opposite side by the projection 1035 formed on the inner surface of the handle. Moreover, as described above, the batteries 1074 are also retained in their position by the sidewalls 1040 shown in FIGS. 11A-11B. The projection 1035 may be shaped as a beam with a plurality of ribs traversing the beam, as shown in FIGS. 11C and 12B. However, the shape of the projection 1035 may vary depending on the type of batteries used and the arrangement of the batteries in the housing 1062.

As shown in FIG. 11D, in the retained state, the battery compartment 1060 is locked in place relative to the rear face plate 1037 by a locking mechanism. In the illustrative embodiment shown in FIG. 11, the locking mechanism is a snap arm 1037d formed at a top portion of the rear faceplate 1037 which includes an arm having some flexibility/elasticity and a lock tooth which engages with the bottom surface of the battery compartment 1060. In this way, the top surface of the housing 1062 of the battery compartment prevents the battery compartment from moving in an upward direction relative to the rear faceplate 1037 and the snap arm 1037d prevent the battery compartment 1060 from moving in a downward direction relative to the rear faceplate 1037. Alternatively, a notch may be provided in the bottom portion of the battery compartment 1060 for engagement with the snap arm 1037d so as to prevent movement of the battery compartment. FIG. 13 shows a more detailed view of the snap arm 1037d, which is formed in the rear faceplate 1037 and extends into the through recess 1037c in the rear faceplate 1037. In some embodiments, instead of the snap arm or in addition to the snap arm, other mechanical engagements may be used to retain the battery compartment in the retained state and in the ejected state. For example, the button 1064 may include a lip formed at or near its top surface, with the periphery of the lip being greater than the opening in the shelf 1038. The lip would prevent the button 1064 from being pushed through the opening in the shelf 1038 past the lip and from falling out together with the batteries. Other types of retaining means may be used for preventing the battery compartment from falling out when the button is moved to the ejected state.

As also shown in FIG. 11D, the operating member 1064 includes a notch 1064a or a recess in its surface that faces the rear faceplate 1037 when assembled. This notch 1064a engages the snap arm 1037d in the ejected state to prevent removal of the battery compartment 1060 from the speculum. When sufficient force is applied to the operating member 1064 in the retained state, the snap arm 1037d disengages from the bottom of the housing 1062 and the battery compartment 1060 is moved from the retaining state to the ejected state shown in FIGS. 12A-12C.

Figure 12A:
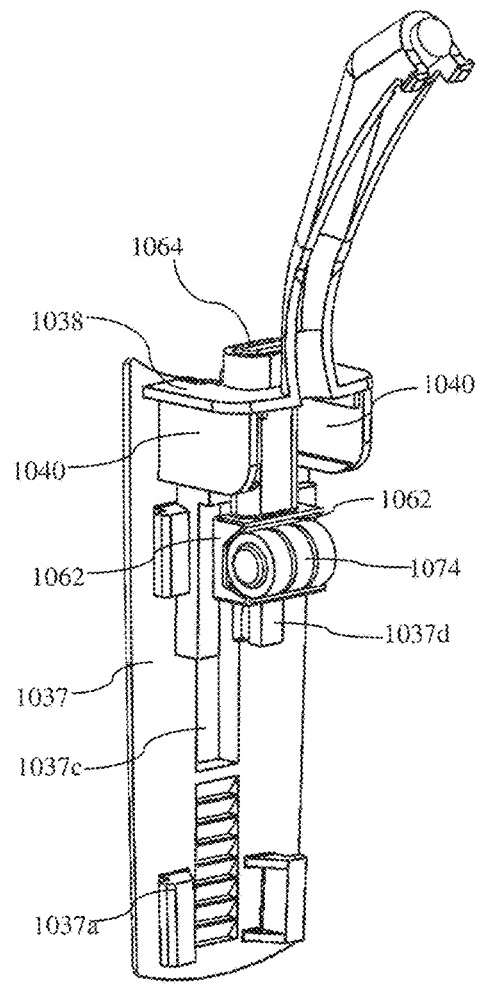
FIGS. 12A-12C show the seventh embodiment of the battery removal mechanism of FIGS. 10A-10B with the battery compartment in an ejected state.
Figure 12B:
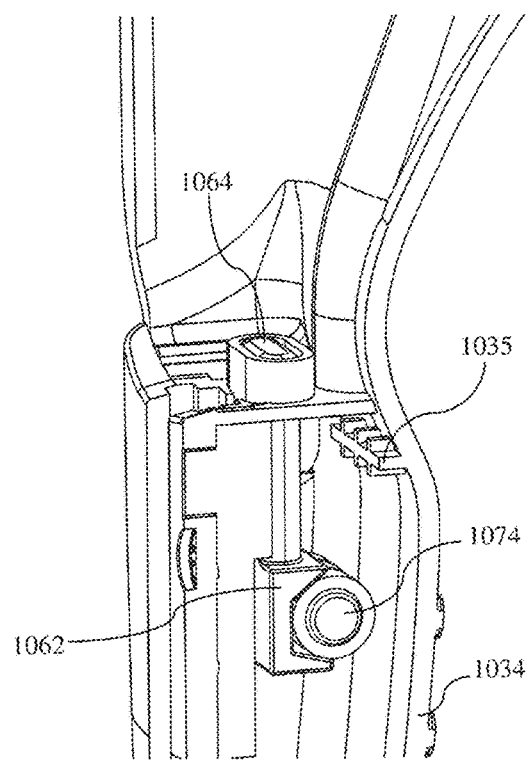
Figure 12C:
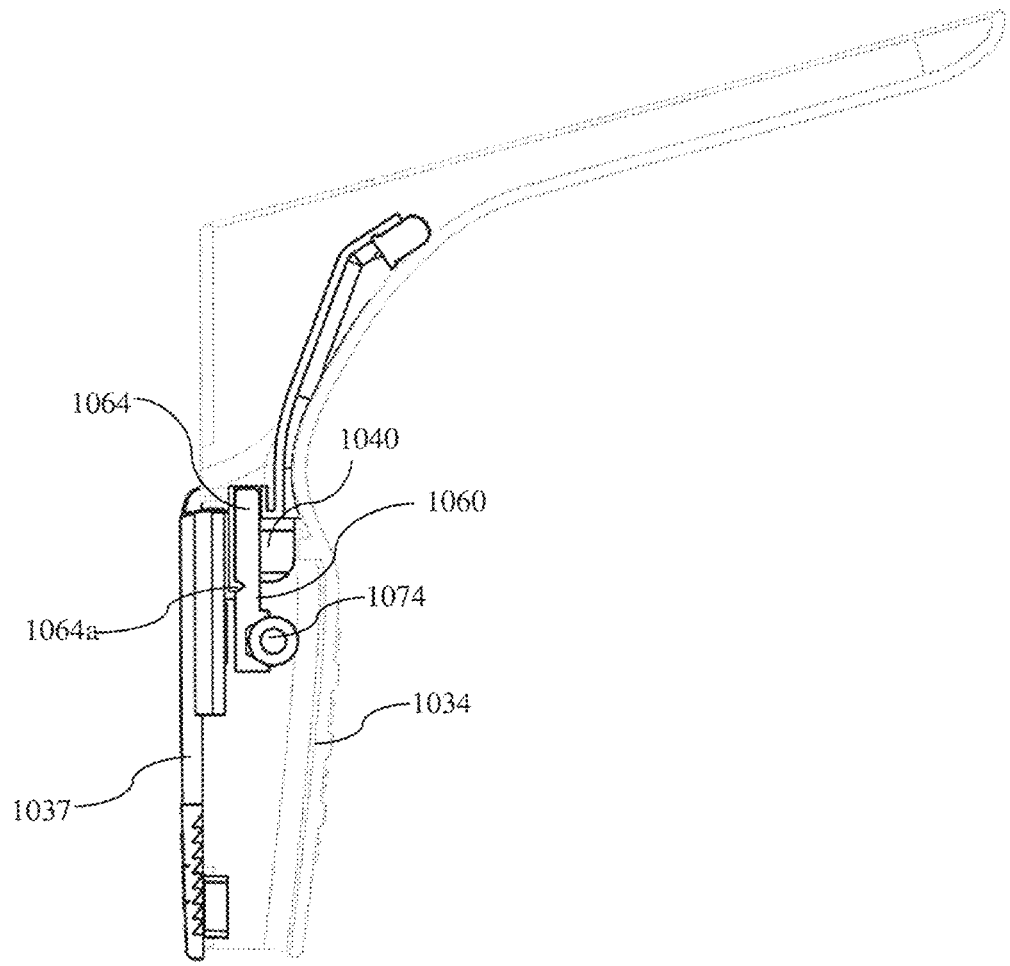
Figure 13:
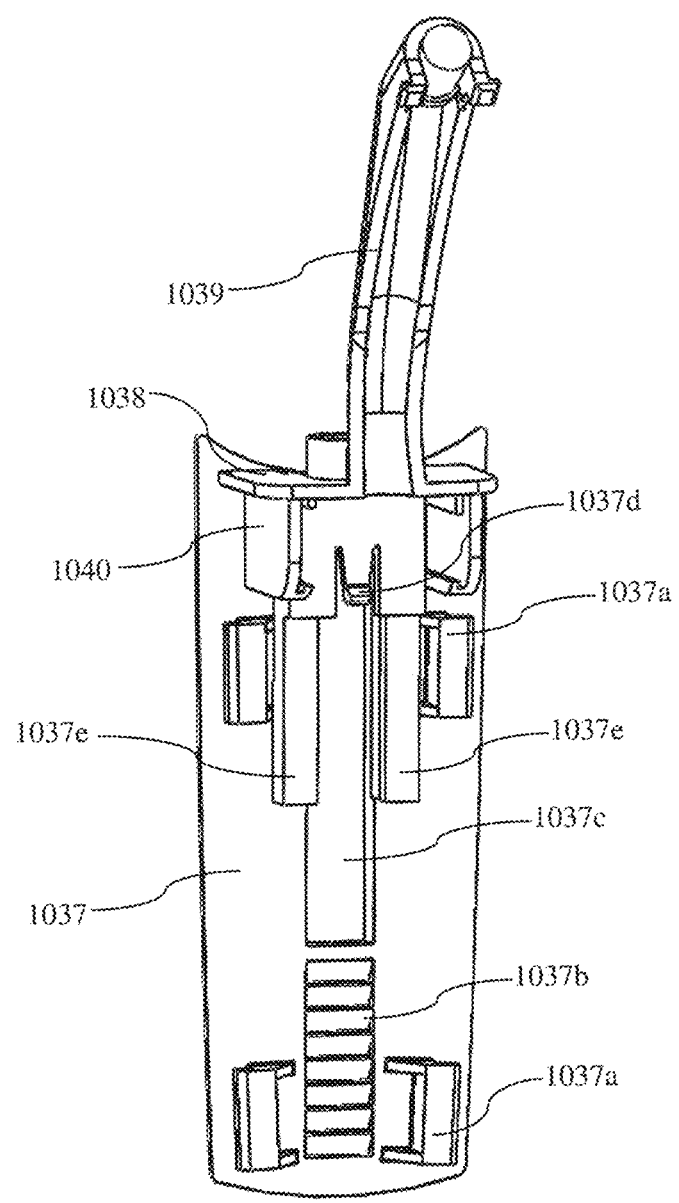
FIG. 13 shows a rear faceplate portion of the medical device of FIGS. 11A-11D without the battery compartment.

FIG. 12A shows the rear face plate assembly 1036 together with the battery compartment 1060 in the ejected state, and FIGS. 12B-12C show a cross-sectional view of the speculum 1000 with the battery compartment 1060 in the ejected state. As can be seen in FIGS. 12A-12C, in the ejected state, the batteries 1074 are no longer pressed against the projection 1035 on the inner surface of the handle and are removed from the space between the sidewalls 1040 that extend from the shelf 1038. Since the batteries are no longer retained on all sides by the housing 1062, the sidewalls 1040 and the projection 1035, they can be easily dislodged from the housing 1062 and removed from the open bottom end of the handle 1034. In the present illustrative embodiment, the handle 1034 is shaped so that the handle is smaller in circumference in the area of the projection 1035 and larger in circumference in the area below the projection 1035. As shown in FIGS. 12B and 12C, the front wall of the handle protrudes outwardly below the projection 1035. This configuration provides additional space for releasing the batteries from the housing 1062 and for allowing the batteries to easily fall through the handle to be removed from the bottom opening in the handle. Thus, in the ejected state, the batteries are removed from the open bottom end of the handle 1034 without requiring physical contact between the user and the batteries, and also without the batteries coming into physical contact with external surfaces of the speculum which may be contaminated with biohazardous materials.

Moreover, as can be seen in FIG. 12C, the battery compartment 1060 is locked in place in the ejected state by the snap arm 1037d, which is engaged with the notch 1064a in the operating member 1064. This prevents removal of the battery compartment 1060 together with the batteries, which could contaminate the batteries with biological materials and would require subsequent separation of the battery compartment from the batteries to be recycled. In addition, the locking of the battery compartment 1060 also inhibits the battery compartment from being returned to the retained state from the ejected state.

Moreover, as can be seen in FIGS. 12A-12B, the operating member 1064 is pressed or pushed by the user into the proximal end of the handle to move the battery compartment into the ejected position. As a result, the user is prevented from accessing the operating member 1064 and from returning the operating member 1064 and the battery compartment 1060 to the retained state. These features which inhibit the battery compartment from returning to the retained state prevent reloading or replacement of the batteries and prevent reuse of the speculum, thus making it truly a disposable and one-time use device.

Although the batteries in the embodiment of FIGS. 10-12 are removed though the open bottom end of the handle, other variations are also contemplated. For example, the batteries may be removed from a cutout formed in one of the sidewalls of the handle 1034 or from a cutout formed in the rear faceplate 1037. In addition, the operating member 1064 in the embodiments of FIGS. 10-12 is configured as a push-button. In other embodiments, a pulling mechanism may instead be used to pull the battery compartment 1060 downward so as to release the batteries from the battery compartment.

Moreover, as discussed above, although FIGS. 10-12 show the battery removal mechanism being used in a speculum, it is understood that this mechanism may be adapted for use in other devices, such as retractors, laryngoscopes, anoscopes, suction devices, electrocautery pens and other medical devices which use batteries, whether or not the batteries are used for an illumination assembly or any other type of battery operated assembly. For example, the battery removal mechanism may be adapted for use in a surgical retractor or laryngoscope by omitting the upper member 1020 and the linear support member 1050 and using a substantially the same mechanism for battery removal in a retractor or laryngoscope that includes a handle 1034, a blade extending at an angle with respect to the handle and the rear faceplate assembly 1036 as described above (similar to FIG. 10B). In another example, the battery removal mechanism may be adapted for use in an anoscope by omitting the upper member 1020 and the linear support member 1050 and by modifying the shape of the lower blade.

Figure 14A:
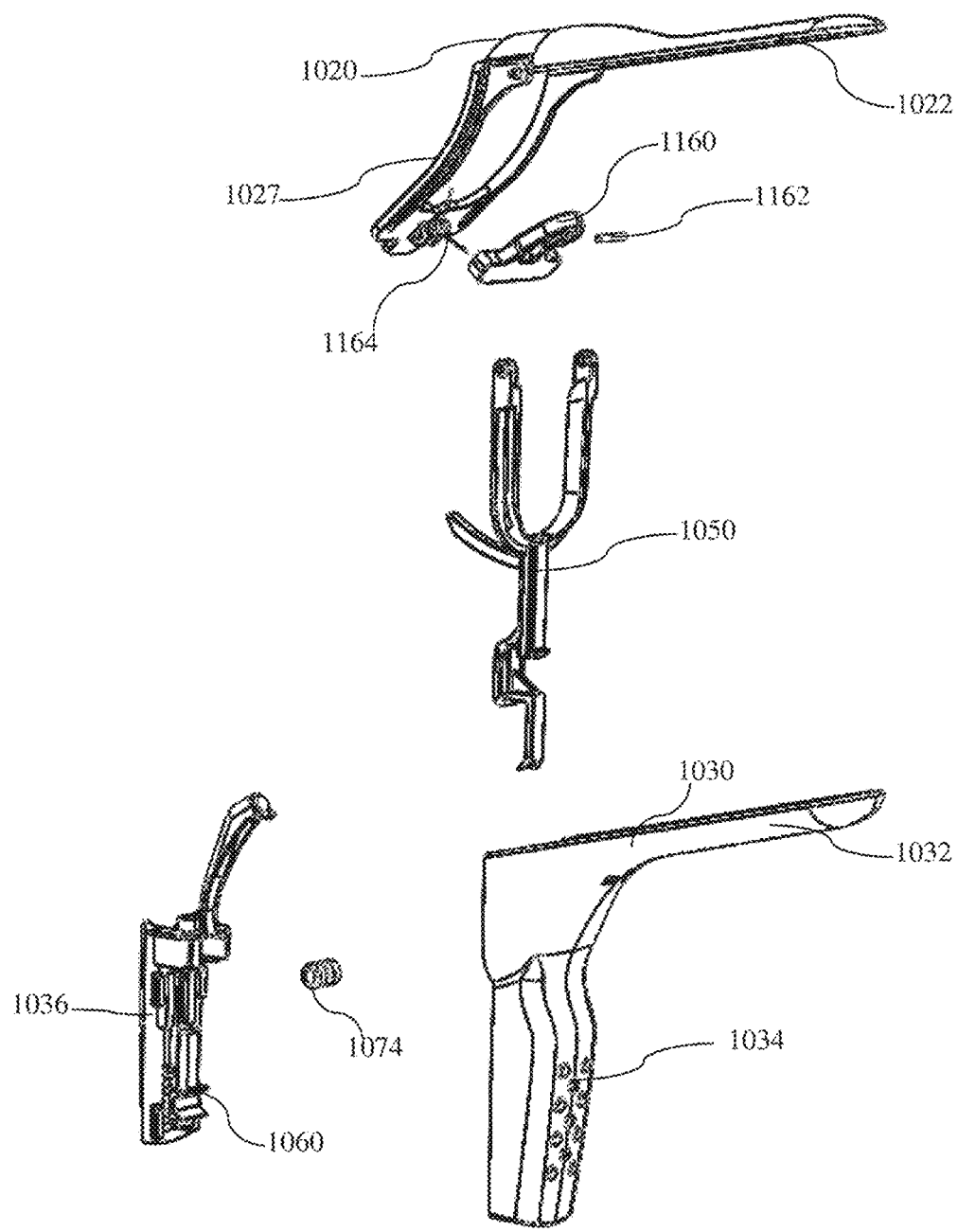
FIG. 14A shows an exploded view of the medical device of FIGS. 10A-13.

The illustrative embodiment of the speculum in FIGS. 10-13 is assembled as shown in FIGS. 14A-14G. FIG. 14A shows an exploded view of the speculum, which includes the lower member 1030 with the handle 1034 and the lower blade 1032, the upper member 1020 with the upper blade 1022 and an operating member 1027, the linear support member 1050, the rear faceplate assembly 1036 together with the battery compartment 1060, batteries 1074, a rocker 1160 for angular adjustment, a biasing member 1164 and a pivot pin 1162 for attaching the rocker 1160. FIGS. 14B-14G show an illustrative sequence of assembling the speculum of FIGS. 10-13.

Figure 14B:
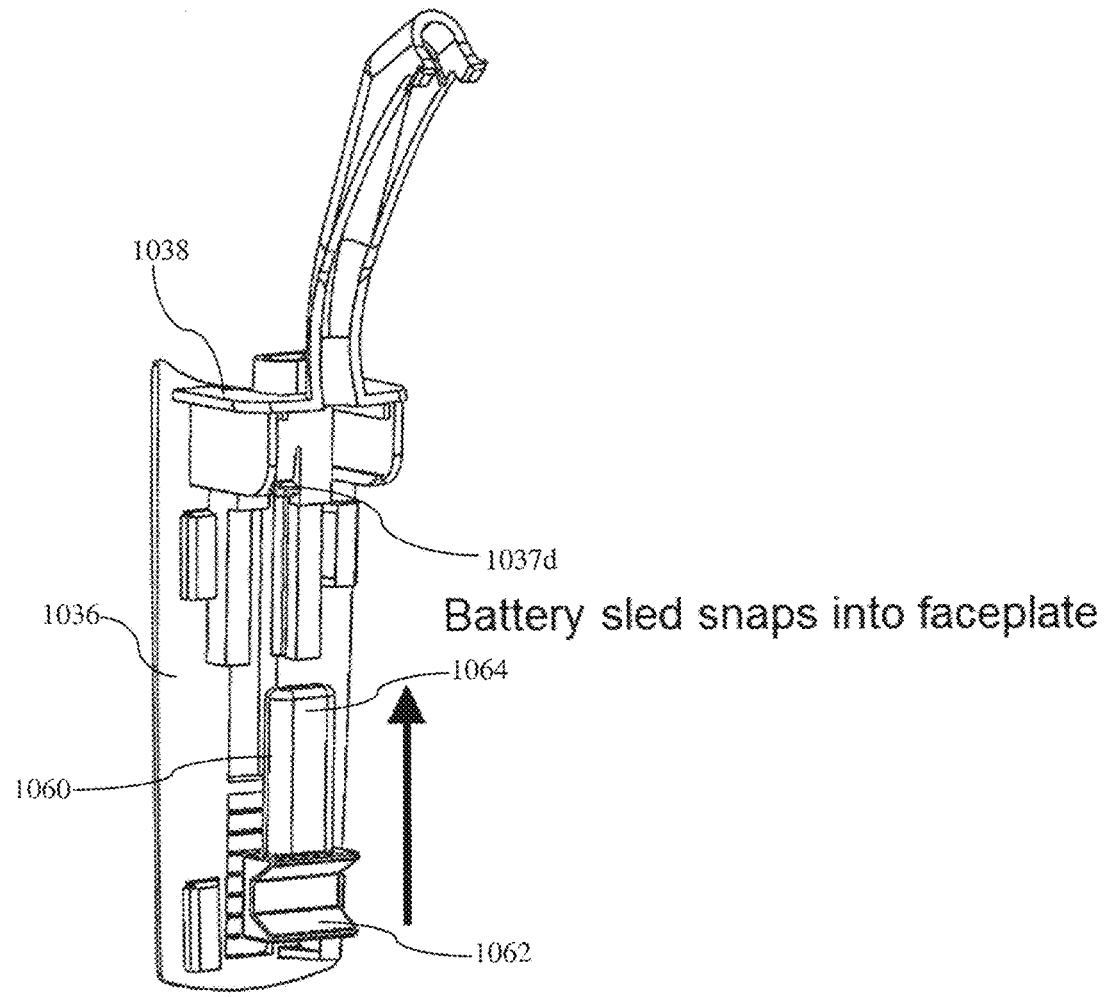
FIGS. 14B-14G show an illustrative sequence of assembling the medical device of FIGS. 10A-13.
Figure 14C:
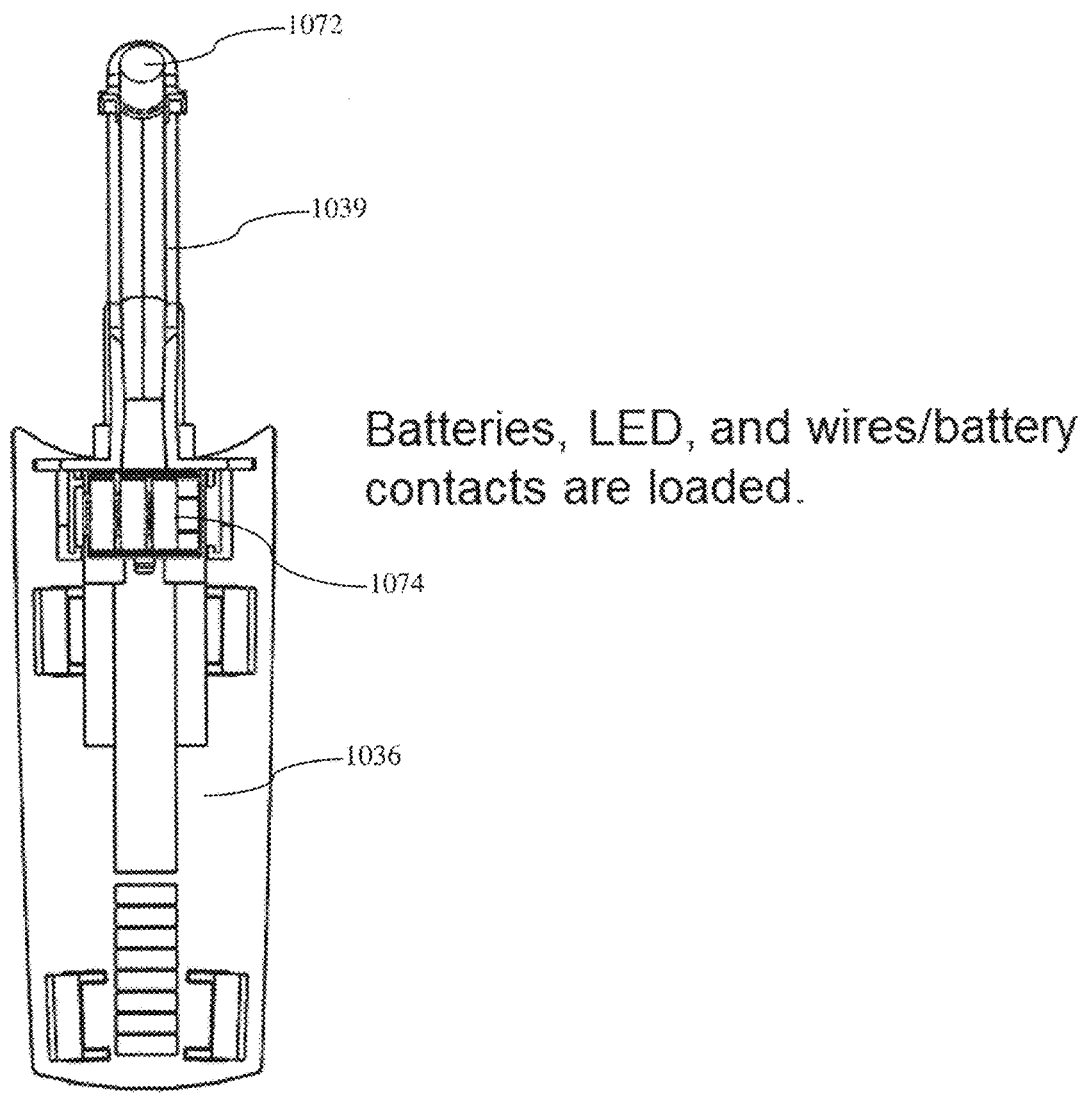

As shown in FIG. 14B, the battery compartment 1060 is assembled with the rear faceplate assembly 1036 by inserting the button 1064 into the opening in the shelf 1038 of the rear faceplate assembly 1036. When the button 1064 is fully inserted into the opening in the shelf 1038, the snap arm 1037d engages with the bottom surface of the housing 1062. After the battery compartment 1060 is snapped in to engage with the rear faceplate assembly 1036, the batteries 1074 are inserted into the housing 1062, as shown in FIG. 14C, and are held by the housing and between the sidewalls 1040 extending from the shelf 1038. At the time of, or prior to, positioning the batteries, battery contacts are loaded to allow for connection of the batteries to wires. In addition, as shown in FIG. 14C, the light source 1072 is positioned to be held by the end of the illumination assembly cover 1039 and the wires are loaded to connect the light source 1072 to the battery contacts and to be enclosed by the illumination assembly cover 1039. As shown in FIG. 14C, the illumination assembly 1070 is assembled together with the rear faceplate assembly 1036 and the battery compartment 1060.

Figure 14D:
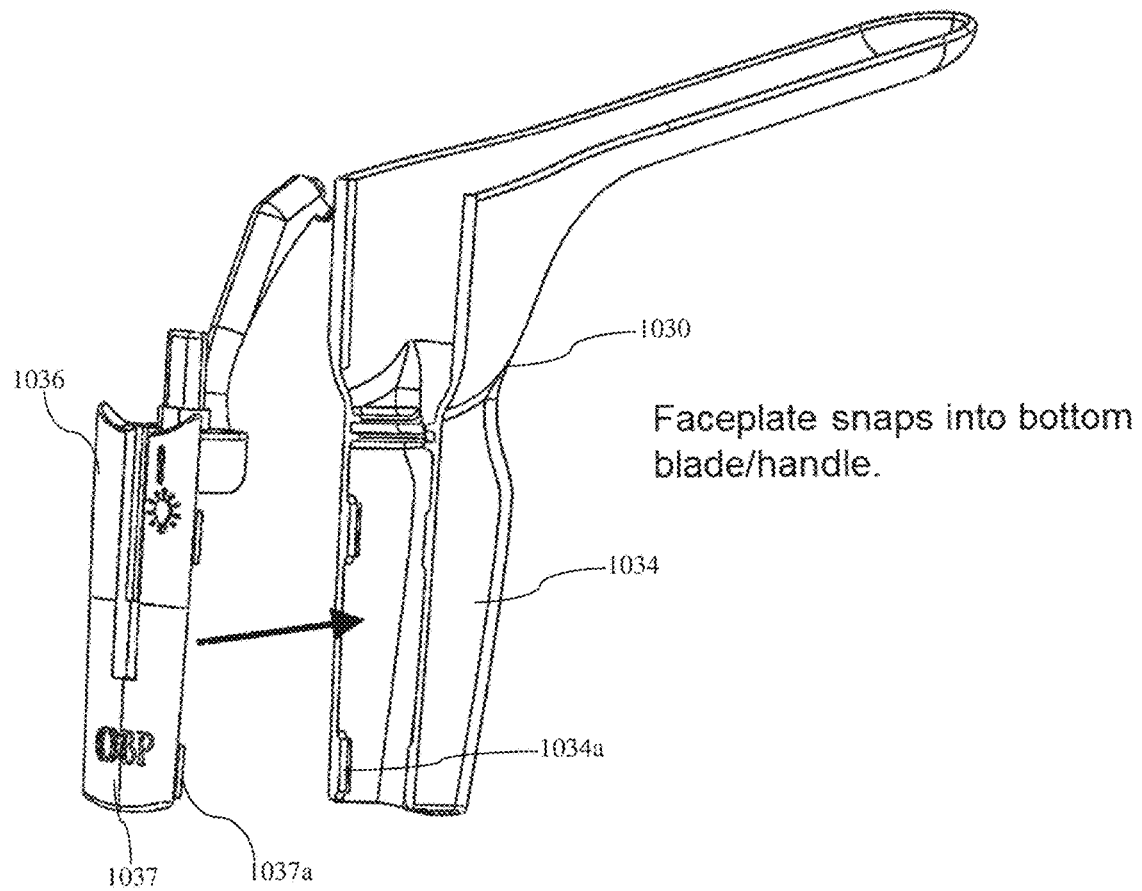

As shown in FIG. 14D, the resulting assembly of FIG. 14C is then assembled together with the lower member 1020. In the illustrative embodiment of FIG. 14D, the rear faceplate assembly 1036 snaps into the rear of the handle 1034 of the lower member 1020 to form the rear wall of the handle 1034. As described above, the engagement protrusions 1037a on the inner surface of the rear faceplate 1037 snap to engage with corresponding protrusions 1034a formed on the inner surface of the handle sidewalls. In other embodiments, other types of engagement may be used for assembling the rear faceplate assembly 1036 with the lower member 1020. For example, the sidewalls of the handle may include channels formed on the inner surfaces thereof for engagement with the engagement protrusions 1037a on the rear faceplate 1037 by sliding the engagement protrusions 1037a into the channels. In other embodiments, the sidewalls of the handle may include recesses for engaging with the engagement protrusions 1037a. In yet other embodiments, the sidewalls of the handle may include protrusions that engage with corresponding recesses formed in the rear faceplate 1037. Other types of engagements may be used for coupling the faceplate assembly 1036 with the lower member 1020.

Figure 14E:
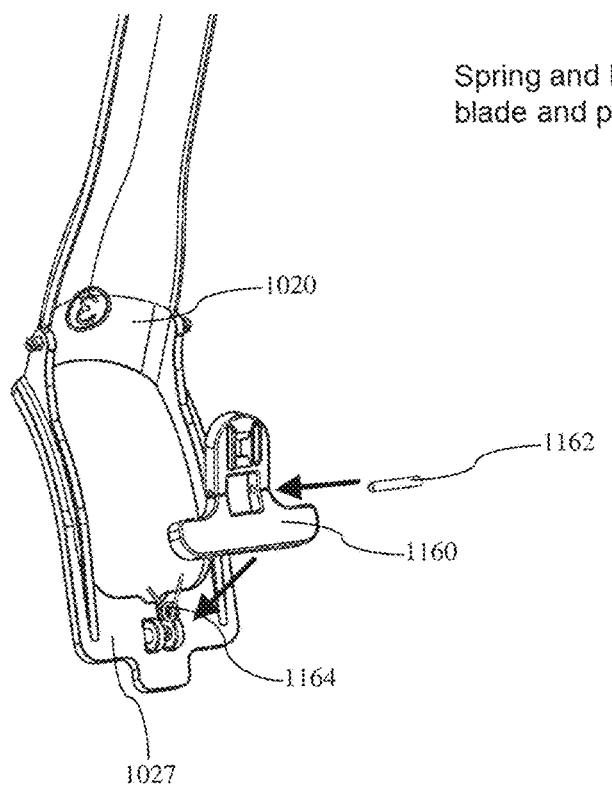

As shown in FIG. 14E, the rocker 1160 of the angular adjustment mechanism is assembled with the operating member 1027. Specifically, the rocker 1160 is positioned with openings therein to align with corresponding openings in the operating member 1027 and a spring 1164 or any other suitable biasing member is positioned between the operating member and the rocker 1160 so as to bias the rocker 1160 in a direction away from the operating member 1027. The pin 1162 is then inserted into the openings in the rocker 1160 and the corresponding openings in the operating member 1027. The ends of the pin 1162 may be flattened or capped to prevent removal of the pin. The biasing member 1164 may be positioned between the operating member 1027 and the rocker 1160 either before or after insertion of the pin to hold the rocker 1160 and the operating member 1027 together.

Figure 14F:
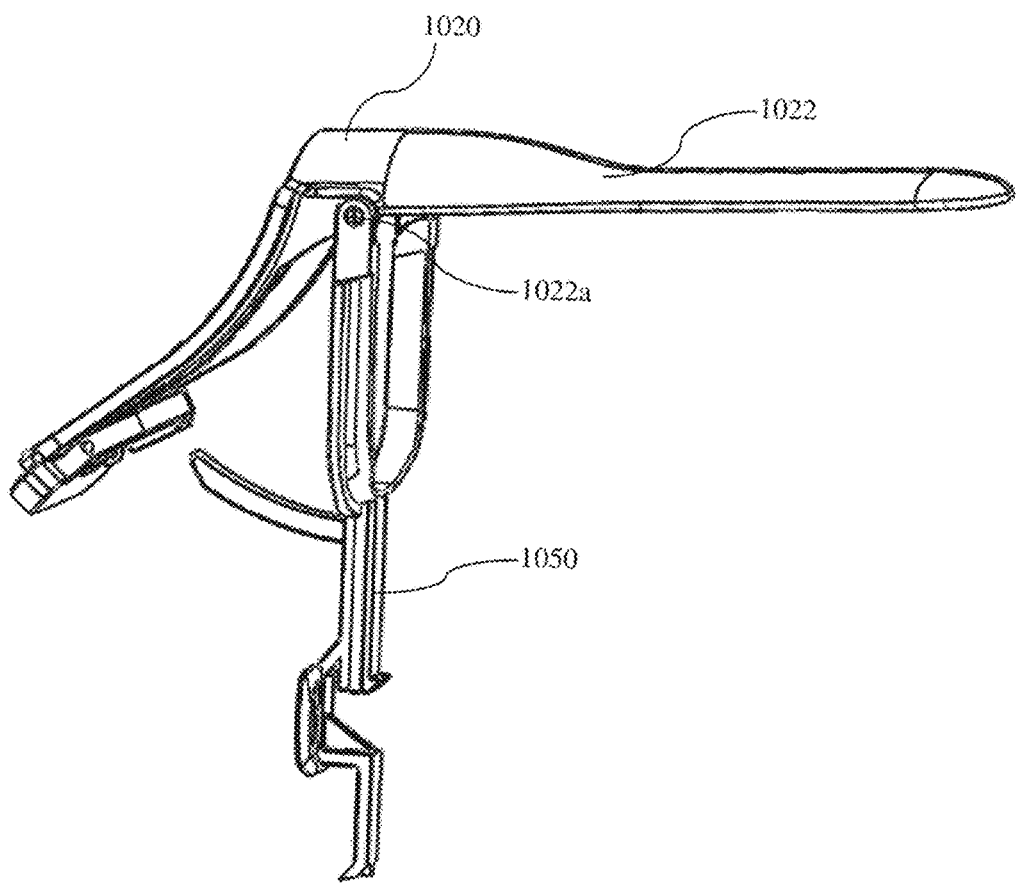
Figure 14G:
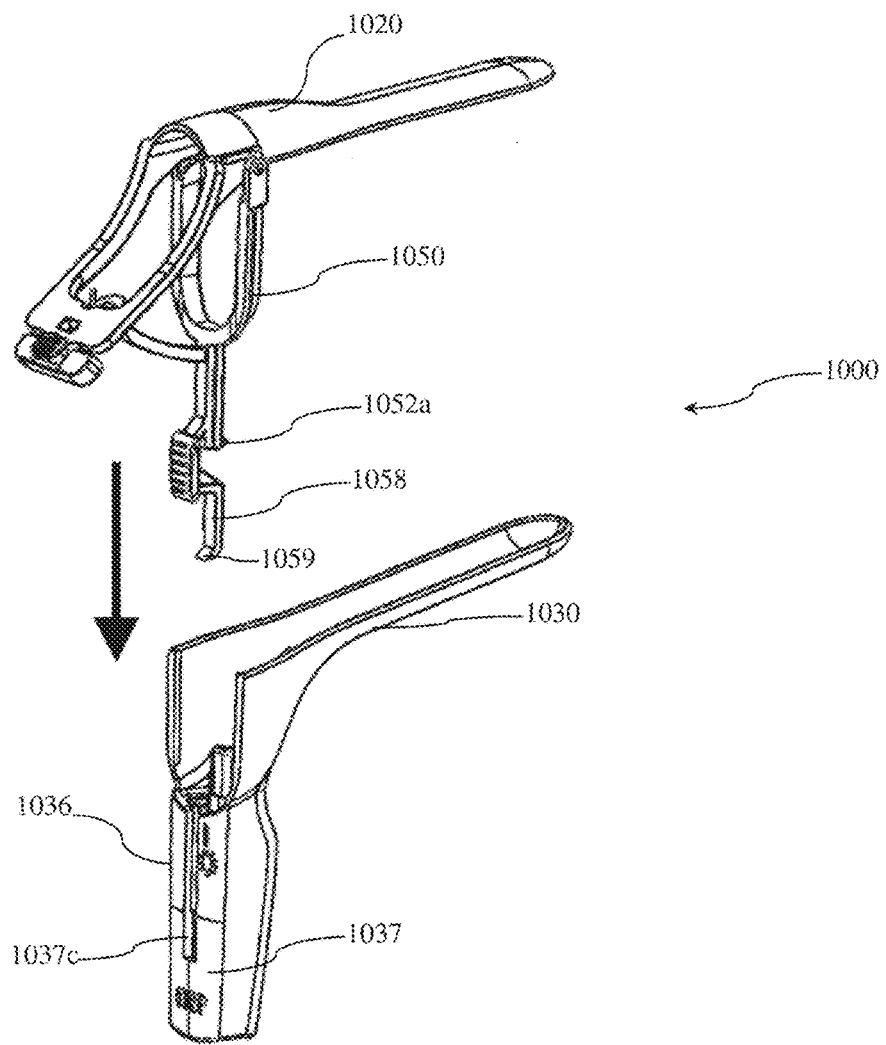

As shown in FIG. 14F, the top member 1020 is assembled together with the linear support member 1050. In the embodiment of FIG. 14F, hinge protrusions 1022a are formed on the outer sides of a proximal end of the upper blade 1022. The linear support member 1050 includes a yoke portion (U-shaped portion) extending from its elongated body with each leg of the yoke portion including an opening for engaging with the corresponding hinge protrusion 1022a. To assemble the upper member 1020 with the linear support member, the hinge protrusions 1022a are snapped into corresponding openings in the yoke portion for a hinge coupling therebetween. In other embodiments, the legs of the yoke portion may include inwardly facing protrusions and the proximal end of the blade 1022 may include corresponding openings for insertion of the protrusions on the yoke portion. Other types of couplings may be used to form a hinge coupling between the upper member 1020 and the linear support member 1050. As shown in FIG. 14G, the top assembly formed in FIG. 14F is then assembled together with the bottom assembly formed in FIG. 14D by inserting the linear support member 1050 into the through recess 1037c formed in the rear faceplate 1037. When the linear support member 1050 is inserted into the through recess 1037c, the engagement arm 1058 of the linear support member 1050 is inserted into the through recess 1037c and slid below the through recess 1037c so that the locking tooth 1059 on the engagement arm 1058 engages with stop tabs formed on the inner surface of the rear faceplate 1037. Also, when the linear support member 1050 is inserted into the through recess 1037c beyond the predetermined position, the retaining projection 1052a on the elongated body 1052 of the linear support member 1050 engages with the rear faceplate assembly 1036 to prevent removal and disengagement of the linear support member 1050 from the rear faceplate assembly 1036. The resulting disposable speculum 1000 has mechanical engagements between the different elements, which makes the speculum easy to assemble and which are sufficiently strong to withstand in-use conditions. The order in which the elements of the speculum 1000 are assembled are not limited to the order shown in FIGS. 14B-14G, and may be varied.

The materials used for forming the medical device of FIGS. 10-14 may be plastic, polymer, metallic or other materials. In certain embodiments, the components of the medical device are formed from plastic materials. Exemplary plastic materials that may be used for constructing the medical device of the present invention include, but are not limited to, polypropylene, polystyrene, and any composite of more than one of these plastics and polymers. The blade member(s), the handle and the rear faceplate assembly may be molded from a colorless transparent or translucent plastic material, such as acrylic plastic, polycarbonate or the like. The rocker used in the speculum described above may be made from the same or similar materials as the speculum or from metallic materials. The linear support member of the speculum described above may be formed from a polyester or polyamide material, such as nylon, or the like. The biasing member(s) (spring) and the pin may be formed from metallic materials or from polymers and plastics. All of these components may be formed by injection molding, extrusion, using a 3D printer or any other suitable technique. In certain embodiments, the materials for forming the medical device, including the blade(s), the handle, the rear faceplate assembly, the rocker and/or the linear support member, of the present invention include glass-fiber reinforced polymers, polyarylamide compounds, thermoplastic crystalline polymers, thermoplastic crystalline polymers of aromatic diamines and aromatic dicarboxylic anhydrides, glass-fiber reinforced polyarylamides, and other materials having sufficient rigidity and strength. Although in the illustrative embodiments, plastic and/or polymer materials are used for the components of the speculum, in other embodiments, some or all of the components may be formed from metallic or fiberglass materials.

Although the embodiments described above are shown with a retractor or a speculum, it is understood that the battery removal mechanisms may be used with other medical devices that use batteries, either as part of the illumination assembly or as part of another assembly that requires batteries. In addition to the specific embodiments described above, other variations may be made for safe removal of batteries without contaminating them with biological (biohazardous) materials, as would be appreciated to those of ordinary skill in the art. Therefore, it is to be understood that other expedients/variations may be employed but that stay within the meaning, scope and spirit of the invention.

This application claims priority to provisional patent application No. 62/649,190 filed on Mar. 28, 2018, 62/574,969 filed on Oct. 20, 2017 and 62/574,412 filed on Oct. 19, 2017, the disclosures of which are incorporated herein by reference.

We claim:

1. A battery-powered medical device comprising:
   an outer housing having an opening formed therein;
   a power source housed within the outer housing, the outer housing being configured to at least partially enclose the power source so as to prevent contamination of the power source with biohazardous materials, and the power source being removable from the outer housing via the opening;
   a cover configured to cover the opening in the outer housing and to retain the power source within the outer housing, and
   an actuator provided within the outer housing that engages with a portion of the power source when the cover covers the opening in the outer housing,
   wherein:
   the cover is configured to be operated by a user to expose the opening in the outer housing,
   when the cover is operated to expose the opening, the actuator is configured to physically remove the power source from the outer housing, the outer housing is configured to release the power source via the opening without requiring physical contact between the user and the power source, and the outer housing is further configured to provide a direct path for release of the power source via the opening, such path providing no contact with contaminated surfaces of the medical device,
   the medical device is one of a speculum, a retractor, an anoscope and a laryngoscope,
   the medical device comprises an illumination assembly including at least one light source and the power source for powering the at least one light source, and
   the outer housing comprises a handle portion and at least one blade portion coupled to the handle portion, with the power source being housed in one of the handle portion and the blade portion.

2. The battery-powered medical device in accordance with claim 1, further comprising a spring biasing the power source in a direction of the cover when the cover covers the opening in the outer housing.

3. The battery-powered medical device in accordance with claim 1, wherein the actuator comprises a band disposed around a portion of the power source and configured to be pulled to release the power source via the opening in the outer housing when the cover is operated to expose the opening.

4. The battery-powered medical device in accordance with claim 1, wherein the medical device is a disposable single-use medical device, the removable power source comprises one or more non-rechargeable single-use batteries, and the outer housing is configured to prevent replacement of the power source after the power source is released therefrom.

5. The battery-powered medical device in accordance with claim 4, wherein:
   the outer housing comprises a handle portion having a first end and a second end;
   the opening in the outer housing is formed in the first end; and
   the power source is housed in the handle portion at a position closer to the second end than to the first end.

6. The battery-powered medical device in accordance with claim 1, wherein:
   the outer housing is a handle portion of the medical device and the medical device further comprises an operative portion coupled to a proximal end of the handle portion;
   a distal end of the handle portion forms the opening in the outer housing; and
   the power source is biased against the cover covering the opening so that when the cover is operated to expose the opening, the removable power source is ejected from the handle portion.

7. The battery-powered medical device in accordance with claim 6, further comprising a lock configured to retain the cover in a first position covering the opening and configured to be operated by the user to release the cover from the first position to a second position so as to expose the opening.

8. The battery-powered medical device in accordance with claim 7, further comprising a compartment for partially enclosing the power source, the compartment being at least partially enclosed by the handle portion and having an open side configured to communicate with the opening in the handle portion,
wherein the cover is engaged with one or more of the compartment and the outer housing.

9. A battery-operated medical device comprising:
an outer housing having an opening formed therein;
a power source housed within the outer housing so as to prevent contamination of the power source with biohazardous materials; and
a holder retained within the outer housing and configured to be movable from a first position to a second position within the outer housing relative to the outer housing, the holder being further configured to partially enclose the power source and to hold the power source within the outer housing when the holder is in the first position, and further configured to release the power source from the outer housing via the opening when the holder is in the second position,
wherein, when the holder is in the second position, the outer housing and the holder are structured to cause the power source to be released from the outer housing while the holder remains connected to the medical device,
wherein the medical device is one of a retractor, a speculum, an anoscope and a laryngoscope, and
wherein the outer housing comprises a handle portion and at least one blade portion extending from the handle portion.

10. The battery-operated medical device in accordance with claim 9, wherein the holder is configured to be inhibited from being moved from the second position to the first position.

11. The battery-operated medical device in accordance with claim 9, wherein when the holder is in the first position, the holder and the outer housing are configured to hold the power source between the holder and an inner wall of the outer housing, and when the holder is in the second position, the holder and the outer housing are configured to release the power source through a space between the holder and the inner wall of the outer housing.

12. The battery-operated medical device in accordance with claim 11, wherein the inner wall of the outer housing includes a projection configured to abut the power source held by the holder in the first position.

13. The battery-operated medical device in accordance with claim 11, wherein the holder has a substantially C-shaped cross-section.

14. The battery-operated medical device in accordance with claim 11, wherein:
the outer housing includes a handle portion having a proximal end and a distal end, with the opening in the outer housing being formed in the distal end of the handle portion, and
the holder is configured to hold the power source within the handle portion in the first position.

15. The battery-operated medical device in accordance with claim 14, wherein in the first position, the holder is configured to hold the power source in the handle portion at a position closer to the proximal end of the handle portion than to the distal end of the handle portion.

16. The battery-operated medical device in accordance with claim 15, further comprising an actuator configured to be operated by a user to move the holder from the first position to the second position and wherein:
the actuator is coupled to the holder and extends from the proximal end of the handle portion in the first position of the holder, and
the actuator is configured to be pushed by the user into the proximal end of the handle portion so as to move the holder to the second position.

17. The battery-operated medical device in accordance with claim 9, wherein the holder comprises a compartment for partially enclosing the power source and having an open side configured to communicate with the opening in the outer housing when the compartment is in the second position, and wherein the compartment is at least partially enclosed by the outer housing.

18. The battery-operated medical device in accordance with claim 17, wherein the compartment includes a sidewall configured to cover the opening in the outer housing when the compartment is in the first position, and wherein the compartment is configured to pivot into the second position so that the open side of the compartment is in communication with the opening in the outer housing.

19. The battery-operated medical device in accordance with claim 18, wherein the outer housing comprises a handle portion, a blade portion and a curved portion connecting the handle portion to the blade portion, and wherein the opening is formed in one of the handle portion, the blade portion and the curved portion.

20. The battery-operated medical device in accordance with claim 9, wherein the medical device comprises an illumination assembly including at least one light source and the power source for powering the at least one light source, and wherein the opening in the outer housing is formed in one of the handle portion and the blade portion.

21. A battery-operated medical device comprising:
an outer housing having an opening formed therein;
a power source housed within the outer housing so as to prevent contamination of the power source with biohazardous materials; and
a holder configured to be movable from a first position to a second position relative to the outer housing, the holder being further configured to partially enclose the power source and to retain the power source within the outer housing when the holder is in the first position, and further configured to release the power source from the outer housing via the opening when the holder is in the second position,
wherein at least one of the outer housing and the holder is configured to prevent replacement of the power source after the power source is released from the outer housing.

22. The battery-operated medical device in accordance with claim 21, wherein:
the outer housing comprises a handle portion having a first end and a second end;
the opening in the outer housing is formed in the first end; and
the power source is housed in the handle portion at a position closer to the second end than to the first end.

23. The battery-operated medical device in accordance with claim 21, wherein the holder is configured to be inhibited from being moved from the second position to the first position.

24. The battery-operated medical device in accordance with claim 23, wherein the outer housing includes a locking projection configured to engage with the holder in the second position to prevent removal of the holder from the outer housing and to inhibit moving of the holder from the second position to the first position.

25. The battery-operated medical device in accordance with claim 23, further comprising an actuator configured to be operated by a user to cause the holder to move from the first position to the second position by pushing the actuator into the outer housing.

26. The battery-operated medical device in accordance with claim 21, wherein:
the medical device is one of a retractor, a speculum, an anoscope and a laryngoscope;
the medical device comprises an illumination assembly including at least one light source and the power source for powering the at least one light source; and
the outer housing comprises a handle portion and at least one blade portion coupled to the handle portion, with the power source being housed in one of the handle portion and the blade portion.

27. A battery-operated medical device comprising:
an outer housing having an opening formed therein;
a power source housed within the outer housing so as to prevent contamination of the power source with bio-hazardous materials; and
a holder configured to be movable from a first position to a second position relative to the outer housing, the holder further being configured to partially enclose the power source and to hold the power source within the outer housing when the holder is in the first position, and further configured to release the power source from the outer housing via the opening when the holder is in the second position,
wherein the holder is configured to be inhibited from being moved from the second position to the first position.

28. The battery-operated medical device in accordance with claim 27, wherein:
the medical device is one of a retractor, a speculum, an anoscope and a laryngoscope;
the medical device comprises an illumination assembly including at least one light source and the power source for powering the at least one light source; and
the outer housing comprises a handle portion and at least one blade portion coupled to the handle portion, with the power source being housed in one of the handle portion and the blade portion.

\* \* \* \* \*